(12) United States Patent
Dubost et al.

(10) Patent No.: US 9,878,985 B2
(45) Date of Patent: Jan. 30, 2018

(54) BENZOCYCLOBUTANE(THIO) CARBOXAMIDES

(71) Applicant: BAYER CROPSCIENCE AKTIENGESELLSCHAFT, Monheim am Rhein (DE)

(72) Inventors: Christophe Dubost, La Tour de Salvagny (FR); Ulrike Wachendorff-Neumann, Neuwied (DE); Philipp Winter, Duesseldorf (DE); Stephane Brunet, St Andre de Corcy (FR); Jean-Pierre Vors, Sainte Foy les Lyon (FR); Cyril Montagne, Monheim am Rhein (DE)

(73) Assignee: BAYER CROPSCIENCE AKTIENGESELLSCHAFT, Monheim Am Rhein (DE)

( * ) Notice: Subject to any disclaimer, the term of this patent is extended or adjusted under 35 U.S.C. 154(b) by 0 days.

(21) Appl. No.: 15/031,456

(22) PCT Filed: Oct. 28, 2014

(86) PCT No.: PCT/EP2014/073121
§ 371 (c)(1),
(2) Date: Apr. 22, 2016

(87) PCT Pub. No.: WO2015/063086
PCT Pub. Date: May 7, 2015

(65) Prior Publication Data
US 2016/0264529 A1    Sep. 15, 2016

(30) Foreign Application Priority Data
Oct. 30, 2013  (EP) .................................... 13190796

(51) Int. Cl.
| | |
|---|---|
| *C07D 231/16* | (2006.01) |
| *A01N 43/40* | (2006.01) |
| *A01N 43/56* | (2006.01) |
| *A01N 45/00* | (2006.01) |
| *C07C 211/60* | (2006.01) |
| *C07D 213/82* | (2006.01) |
| *C07C 211/61* | (2006.01) |
| *C07C 25/22* | (2006.01) |
| *C07C 17/23* | (2006.01) |
| *C07C 17/275* | (2006.01) |
| *C07C 209/62* | (2006.01) |
| *C07D 231/14* | (2006.01) |

(52) U.S. Cl.
CPC .......... *C07D 231/16* (2013.01); *A01N 43/40* (2013.01); *A01N 43/56* (2013.01); *A01N 45/00* (2013.01); *C07C 17/23* (2013.01); *C07C 17/275* (2013.01); *C07C 25/22* (2013.01); *C07C 209/62* (2013.01); *C07C 211/60* (2013.01); *C07C 211/61* (2013.01); *C07D 213/82* (2013.01); *C07D 231/14* (2013.01); *C07C 2602/06* (2017.05); *C07C 2603/94* (2017.05)

(58) Field of Classification Search
None
See application file for complete search history.

(56) References Cited

U.S. PATENT DOCUMENTS

| | | | |
|---|---|---|---|
| 5,093,347 A * | 3/1992 | Graneto | ................. A01N 43/56 514/406 |
| 2011/0124698 A1 | 5/2011 | Dunkel et al. | |
| 2013/0231303 A1 | 9/2013 | Benting et al. | |

FOREIGN PATENT DOCUMENTS

| | | |
|---|---|---|
| EP | 0199822 A1 | 11/1986 |
| EP | 0276177 A1 | 7/1988 |
| JP | S-6296472 A | 5/1987 |
| JP | H-01313402 A | 12/1989 |
| JP | H-05310512 A | 11/1993 |
| WO | 9212970 A1 | 8/1992 |
| WO | 02059086 A1 | 8/2002 |
| WO | 02096882 A1 | 12/2002 |
| WO | 2004103975 A1 | 12/2004 |
| WO | 2012065945 A1 | 5/2012 |

OTHER PUBLICATIONS

Khrapunovich, Marina. J. Org. Chem. (2007) 72(20) 7574-7580.*

* cited by examiner

*Primary Examiner* — Deepak R Rao
*Assistant Examiner* — Laura M Daniel
(74) *Attorney, Agent, or Firm* — McBee Moore Woodward & Vanik IP, LLC

(57) ABSTRACT

The present invention relates to novel benzocyclobutane (thio) carboxamides, to processes for preparing these compounds, to compositions comprising these compounds, and to the use thereof as biologically active compounds, especially for control of harmful microorganisms in crop protection and in the protection of materials.

12 Claims, No Drawings

BENZOCYCLOBUTANE(THIO) CARBOXAMIDES

CROSS REFERENCE TO RELATED APPLICATIONS

This application is a §371 National Stage Application of PCT/EP2014/073121, filed 28 Oct. 2014 which claims priority to EP 13190796.6, filed 30 Oct. 2013.

BACKGROUND

Field of the Invention

The present invention relates to novel benzocyclobutane (thio) carboxamides, to processes for preparing these compounds, to compositions comprising these compounds, and to the use thereof as biologically active compounds, especially for control of harmful microorganisms in crop protection and in the protection of materials.

Description of Related Art

It is already known that certain indanyl carboxamides have fungicidal properties (e.g. WO 1992/12970, EP-A 0 199 822, EP-A 0 276 177, JP-A 62-096472, JP-A 05-310512, JP-A 01-313402, WO 2002/059086, WO 2004/103975 and *J. Org. Chem.* 1995, 60, 1626-1631).

Certain tetrahydronaphtyl carboxamides are also known (J. Pesticide Sci. 18, 49-57, 1993, WO 2012/065945, WO 2002/096882). WO 2004/103975 describes in general iodopyrazole tetrahydronaphthyl carboxamides without mentioning concrete examples.

Since the ecological and economic demands made on modern active ingredients, for example fungicides, are increasing constantly, for example with respect to activity spectrum, toxicity, selectivity, application rate, formation of residues and favorable manufacture, and there can also be problems, for example, with resistances, there is a constant need to develop novel fungicidal compositions which have advantages over the known compositions at least in some areas.

SUMMARY

This invention now provides novel benzocyclobutane (thio) carboxamides of the formula (I)

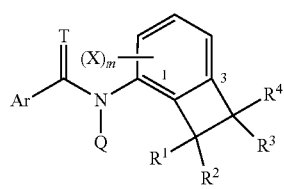

(I)

in which

Ar represents a radical selected from the group Ar1 to Ar15:

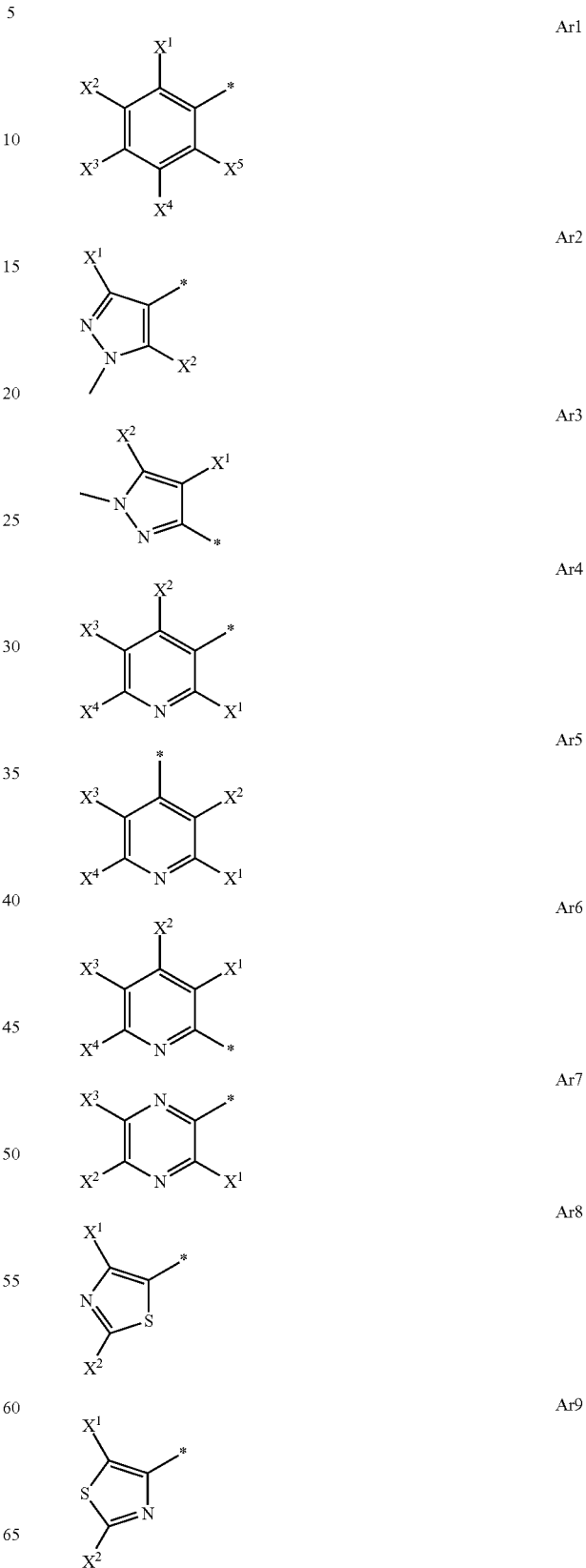

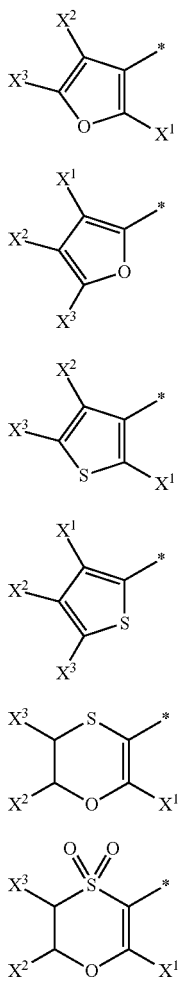

Ar10

Ar11

Ar12

Ar13

Ar14

Ar15

$X^1$, $X^2$, $X^3$, $X^4$ and $X^5$ independently represent hydrogen; halogen; cyano; nitro, hydroxyl; $C_1$-$C_{16}$-alkyl, $C_1$-$C_6$-haloalkyl having 1 to 9 identical or different halogen atoms; $C_3$-$C_7$-cycloalkyl, $C_3$-$C_7$-halocycloalkyl having 1 to 9 identical or different halogen atoms; $C_1$-$C_6$-alkoxy; $C_1$-$C_6$-haloalkoxy having 1 to 9 identical or different halogen atoms;

T represents an oxygen or sulfur atom;

Q represents hydrogen, $C_1$-$C_6$-alkylsulfonyl, $C_1$-$C_4$-alkoxy-$C_1$-$C_4$-alkyl, $C_1$-$C_4$-haloalkylsulfonyl, halo-$C_1$-$C_4$-alkoxy-$C_1$-$C_4$-alkyl;

X represents halogen, nitro, cyano, $C_1$-$C_{12}$-alkyl; $C_1$-$C_6$-haloalkyl having 1 to 9 identical or different halogen atoms; $C_1$-$C_6$-alkoxy; $C_1$-$C_6$-haloalkoxy having 1 to 9 identical or different halogen atoms; $C_1$-$C_6$-alkylsulfanyl; $C_1$-$C_6$-haloalkylsulfanyl having 1 to 9 identical or different halogen atoms; $C_1$-$C_6$-alkylsulfinyl; $C_1$-$C_6$-haloalkylsulfinyl having 1 to 9 identical or different halogen atoms; $C_1$-$C_6$-alkylsulfonyl; $C_1$-$C_6$-haloalkylsulfonyl having 1 to 9 identical or different halogen atoms; $C_2$-$C_{12}$-alkenyl; $C_2$-$C_{12}$-alkynyl; $C_3$-$C_7$-cycloalkyl; phenyl; tri($C_1$-$C_8$)alkylsilyl; tri($C_1$-$C_8$)alkylsilyl-$C_1$-$C_8$-alkyl;

m represents 0, 1, 2 or 3;

$R^1$, $R^2$, $R^3$ and $R^4$ independently one to another represent hydrogen; halogen; $C_1$-$C_{16}$-alkyl; $C_2$-$C_{16}$-haloalkyl having 1 to 9 identical or different halogen atoms; $C_3$-$C_8$-cycloalkyl; $C_3$-$C_7$-halocycloalkyl having 1 to 9 identical or different halogen atoms; $C_1$-$C_6$-haloalkyl having 1 to 9 identical or different halogen atoms; ($C_3$-$C_8$-cycloalkyl)-$C_1$-$C_5$-alkyl; ($C_3$-$C_8$-cycloalkyl)-$C_3$-$C_8$-cycloalkyl; $C_2$-$C_{16}$-alkenyl; $C_2$-$C_{16}$-alkynyl; $C_2$-$C_{16}$-alkenyl-$C_1$-$C_{16}$-alkyl; $C_2$-$C_{16}$-alkynyl-$C_1$-$C_{16}$-alkyl; $C_1$-$C_{16}$-alkoxy; $C_3$-$C_8$-cycloalkyloxy; ($C_3$-$C_8$-cycloalkyl)-$C_1$-$C_8$-alkyloxy; $C_1$-$C_8$-alkylsulfanyl; $C_3$-$C_8$-cycloalkylsulfanyl; ($C_3$-$C_8$-cycloalkyl)-$C_1$-$C_8$-alkylsulfanyl; $C_2$-$C_{16}$-alkenyloxy; $C_3$-$C_8$-alkynyloxy; aryl which is optionally substituted by up to 6 identical or different groups $R^b$; aryl-$C_1$-$C_8$-alkyloxy which is optionally substituted by up to 6 identical or different groups $R^b$; aryl-$C_1$-$C_8$-alkylsulfanyl which is optionally substituted by up to 6 identical or different groups $R^b$; aryloxy which is optionally substituted by up to 6 identical or different groups $R^b$; arylsulfanyl which is optionally substituted by up to 6 identical or different groups $R^b$; ($C_3$-$C_8$-cycloalkyl)-$C_2$-$C_8$-alkenyl; ($C_3$-$C_8$-cycloalkyl)-$C_2$-$C_8$-alkynyl; tri($C_1$-$C_5$)alkylsilyl; tri($C_1$-$C_5$)alkylsilyl-$C_1$-$C_8$-alkyl; aryl-$C_1$-$C_8$-alkyl which is optionally substituted by up to 6 identical or different groups $R^b$; aryl-$C_2$-$C_8$-alkenyl which is optionally substituted by up to 6 identical or different groups $R^b$; aryl-$C_2$-$C_8$-alkynyl which is optionally substituted by up to 6 identical or different groups $R^b$;

provided that $R^1$, $R^2$, $R^3$ and $R^4$ do not simultaneously represent hydrogen or $R^1$ and $R^2$ represent together with the carbon to which they are attached a $C_3$-$C_8$-cycloalkyl; $C_3$-$C_8$-cycloalkenyl, each of which is optionally substituted or $R^1$ and $R^2$ represent a group $=C(Y^1)Y^2$ or $R^1$ and $R^2$ represent a 5 or 6 membered ring containing 1 or 2 heteroatoms and/or $R^3$ and $R^4$ represent together with the carbon to which they are attached a $C_3$-$C_8$-cycloalkyl, $C_3$-$C_8$-cycloalkenyl each of which is optionally substituted and/or $R^3$ and $R^4$ represent a group $=C(Y^1)Y^2$ and/or $R^3$ and $R^4$ represent a 5 or 6 membered ring containing 1 or 2 heteroatoms or $R^1$ and $R^3$ represent with the carbons to which they are attached a $C_3$-$C_8$-cycloalkyl, $C_3$-$C_8$-cycloalkenyl each of which is optionally substituted;

$R^b$ represents halogen; nitro, cyano, $C_1$-$C_{12}$-alkyl; $C_1$-$C_6$-haloalkyl having 1 to 9 identical or different halogen atoms; $C_1$-$C_6$-alkoxy; $C_1$-$C_6$-haloalkoxy having 1 to 9 identical or different halogen atoms; $C_1$-$C_6$-alkylsulfanyl; $C_1$-$C_6$-haloalkylsulfanyl having 1 to 9 identical or different halogen atoms; $C_1$-$C_6$-alkylsulfonyl; $C_1$-$C_6$-haloalkylsulfonyl having 1 to 9 identical or different halogen atoms; $C_2$-$C_{12}$-alkenyl; $C_2$-$C_{12}$-alkynyl; $C_3$-$C_7$-cycloalkyl; phenyl; tri($C_1$-$C_8$)alkylsilyl; tri($C_1$-$C_8$)alkylsilyl-$C_1$-$C_8$-alkyl;

$Y^1$ and $Y^2$ independently of one another represent hydrogen, halogen, $C_1$-$C_{12}$-alkyl; $C_1$-$C_6$-haloalkyl having 1 to 9 identical or different halogen atoms; $C_1$-$C_5$-alkylsulfanyl; phenyl; each of which is optionally substituted; or $Y^1$ and $Y^2$ can form together with the carbon to which they are attached a $C_3$-$C_8$-cycloalkyl or a $C_3$-$C_8$-cycloalkenyl or a saturated 5, 6 or 7 membered heterocycle; each of which is optionally substituted.

DETAILED DESCRIPTION OF A PREFERRED EMBODIMENT

Preferred Embodiments

The formula (I) provides a general definition of the benzocycobutane(thio) carboxamides according to the invention. Preferred radical definitions for the formulae shown above and below are given below. These definitions apply to the end products of the formula (I) and likewise to all intermediates.

Ar preferably represents a radical selected from the groups Ar1, Ar2, Ar4, Ar7, Ar8, Ar10 and Ar13.

Ar particularly preferably represents a radical selected from the groups Ar1, Ar2 and Ar4.

Ar most preferably represents a radical selected from the groups Ar2 and Ar4.

$X^1$ preferably represents halogen; $C_1$-$C_{16}$-alkyl, $C_1$-$C_6$-haloalkyl having 1 to 9 identical or different halogen atoms; $C_3$-$C_7$-cycloalkyl, $C_3$-$C_7$-halocycloalkyl having 1 to 9 identical or different halogen atoms.

$X^1$ particularly preferably represents $C_1$-$C_{12}$-alkyl, $C_1$-$C_4$-haloalkyl having 1 to 9 identical or different halogen atoms.

$X^1$ very particularly preferably represents methyl, ethyl, difluoromethyl, trifluoromethyl, iodine.

$X^1$ most preferably represents difluoromethyl.

$X^2$, $X^3$, $X^4$ and $X^5$ independently from each other preferably represent hydrogen, halogen, $C_1$-$C_{16}$-alkyl, $C_1$-$C_6$-haloalkyl having 1 to 9 identical or different halogen atoms; $C_3$-$C_7$-cycloalkyl, $C_3$-$C_7$-halocycloalkyl having 1 to 9 identical or different halogen atoms.

$X^2$, $X^3$, $X^4$ and $X^5$ particularly preferably independently from each other represent hydrogen, fluorine, chlorine, bromine, iodine; $C_1$-$C_{12}$-alkyl, $C_1$-$C_4$-haloalkyl having 1 to 9 identical or different halogen atoms.

$X^2$, $X^3$, $X^4$ and $X^5$ very particularly preferably independently from each other represent hydrogen, fluorine, chlorine, bromine, iodine, methyl, ethyl.

$X^2$, $X^3$, $X^4$ and $X^5$ most preferably independently from each other represent fluorine, chlorine.

T preferably represents an oxygen atom.

Q preferably represents hydrogen, $C_1$-$C_4$-alkylsulfonyl, $C_1$-$C_3$-alkoxy-$C_1$-$C_3$-alkyl, $C_1$-$C_4$-haloalkylsulfonyl, halo-$C_1$-$C_3$-alkoxy-$C_1$-$C_3$-alkyl having in each case 1 to 9 fluorine, chlorine and/or bromine atoms.

Q particularly preferably represents hydrogen, methylsulfonyl, ethylsulfonyl, n- or isopropylsulfonyl, n-, iso-, sec- or tert-butylsulfonyl, methoxymethyl, methoxyethyl, ethoxymethyl, ethoxyethyl, trifluoromethylsulfonyl, trifluoromethoxymethyl.

Q most preferably represents hydrogen.

X preferably represents fluorine, chlorine, methyl or trifluoromethyl.

X particularly preferably represents fluorine, where fluorine is particularly preferably located in the 4-, 5- or 6-position, very particularly preferably in the 4- or 6-position of the benzocyclobutane radical.

X moreover particularly preferably represents chlorine, where chlorine is particularly preferably located in the 4-5- or 6-position, very particularly preferably in the 4- or 6-position of the benzocyclobutane radical.

X moreover particularly preferably represents methyl, where methyl is particularly preferably located in the 4-5- or 6-position, very particularly preferably in the 4- or 6-position of the benzocyclobutane radical.

X moreover particularly preferably represents trifluorometyl, where trifluorometyl is particularly preferably located in the 4-5- or 6-position, very particularly preferably in the 4- position of the benzocyclobutane radical.

m preferably represents 0, 1 or 2.

m particularly preferably represents 0 or 1.

m most preferably represents 0.

$R^1$, $R^2$, $R^3$ and $R^4$ independently of one another preferably represent hydrogen; halogen; $C_1$-$C_{16}$-alkyl; $C_2$-$C_{16}$-haloalkyl having 1 to 9 identical or different halogen atoms; $C_3$-$C_8$-cycloalkyl; $C_3$-$C_7$-halocycloalkyl having 1 to 9 identical or different halogen atoms; $C_1$-$C_6$-haloalkyl having 1 to 9 identical or different halogen atoms; ($C_3$-$C_8$-cycloalkyl)-$C_1$-$C_8$-alkyl; ($C_3$-$C_8$-cycloalkyl)-$C_3$-$C_8$-cycloalkyl; $C_1$-$C_{16}$-alkoxy; $C_3$-$C_8$-cycloalkyloxy; ($C_3$-$C_8$-cycloalkyl)-$C_1$-$C_8$-alkyloxy; aryl which is optionally substituted by up to 6 identical or different groups $R^b$; aryl-$C_1$-$C_8$-alkyloxy which is optionally substituted by up to 6 identical or different groups $R^b$; aryl-$C_1$-$C_8$-alkyl which is optionally substituted by up to 6 identical or different groups $R^b$;

provided that $R^1$, $R^2$, $R^3$ and $R^4$ do not simultaneously represent hydrogen.

$R^1$, $R^2$, $R^3$ and $R^4$ independently of one another particularly preferably represent hydrogen; halogen; $C_1$-$C_{16}$-alkyl; $C_2$-$C_{16}$-haloalkyl having 1 to 9 identical or different halogen atoms; $C_3$-$C_8$-cycloalkyl; $C_3$-$C_7$-halocycloalkyl having 1 to 9 identical or different halogen atoms; $C_1$-$C_6$-haloalkyl having 1 to 9 identical or different halogen atoms; ($C_3$-$C_8$-cycloalkyl)-$C_1$-$C_8$-alkyl; ($C_3$-$C_8$-cycloalkyl)-$C_3$-$C_8$-cycloalkyl; $C_1$-$C_{16}$-alkoxy; aryl which is optionally substituted by up to 6 identical or different groups $R^b$; aryl-$C_1$-$C_8$-alkyl which is optionally substituted by up to 6 identical or different groups $R^b$;

provided that $R^1$, $R^2$, $R^3$ and $R^4$ do not simultaneously represent hydrogen.

$R^1$, $R^2$, $R^3$ and $R^4$ independently of one another most preferably represent hydrogen; phenyl, ethyl, methyl, propan-2-yl;

provided that $R^1$, $R^2$, $R^3$ and $R^4$ do not simultaneously represent hydrogen.

$R^1$ and $R^2$ represents preferably together with the carbon to which they are attached an optionally substituted $C_3$-$C_8$-cycloalkyl where the substituents can be chosen from halogen and $C_1$-$C_6$-alkyl.

$R^1$ and $R^2$ represents particularly preferably together with the carbon to which they are attached an optionally substituted cyclopropyl, cyclobutyl, cyclopentyl, cyclohexyl where the substituents can be chosen from fluorine, chlorine, methyl and ethyl.

$R^3$ and $R^4$ represents preferably together with the carbon to which they are attached an optionally substituted $C_3$-$C_8$-cycloalkyl where the substituents can be chosen from halogen and $C_1$-$C_6$-alkyl.

$R^3$ and $R^4$ represents particularly preferably together with the carbon to which they are attached an optionally substituted cyclopropyl, cyclobutyl, cyclopentyl, cyclohexyl where the substituents can be chosen from fluorine, chlorine, methyl and ethyl.

$R^3$ and $R^4$ represents most preferably together with the carbon to which they are attached cyclopentyl or cyclohexyl.

$R^1$ and $R^3$ represents preferably together with the carbons to which they are attached an optionally substituted $C_3$-$C_8$-cycloalkyl where the substituents can be chosen from halogen and $C_1$-$C_6$-alkyl.

$Y^1$ and $Y^2$ preferably independently of one another represent hydrogen, halogen, $C_1$-$C_{12}$-alkyl, $C_1$-$C_6$-haloalkyl having 1 to 9 identical or different halogen atoms or form together with the carbon to which they are attached an optionally substituted cyclopropyl, cyclobutyl, cyclopentyl, cyclohexyl.

$Y^1$ and $Y^2$ particularly preferably independently of one another represent hydrogen, fluorine, chlorine, bromine, methyl; ethyl, propyl, isopropyl.

$R^b$ preferably represents halogen, nitro, cyano, $C_1$-$C_8$-alkyl; $C_1$-$C_4$-haloalkyl having 1 to 9 identical or different halogen atoms; $C_1$-$C_6$-alkoxy; $C_1$-$C_4$-haloalkoxy having 1 to 9 identical or different halogen atoms; $C_1$-$C_6$-alkylsulfanyl; $C_1$-$C_4$-haloalkylsulfanyl having 1 to 9 identical or different halogen atoms; $C_1$-$C_6$-alkylsulfonyl; $C_1$-$C_4$-haloalkylsulfonyl having 1 to 9 identical or different halogen atoms; $C_2$-$C_8$-alkenyl; $C_2$-$C_8$-alkynyl; $C_3$-$C_6$-cycloalkyl; phenyl; tri($C_1$-$C_6$)alkylsilyl; tri($C_1$-$C_6$)alkylsilyl-$C_1$-$C_6$-alkyl.

$R^b$ particularly preferably represents fluorine, chlorine, bromine; $C_1$-$C_6$-alkyl; $C_1$-$C_4$-haloalkyl having 1 to 9 identical or different halogen atoms; $C_1$-$C_4$-alkoxy; $C_1$-$C_4$-haloalkoxy having 1 to 9 identical or different halogen atoms; $C_1$-$C_4$-alkylsulfanyl; $C_1$-$C_4$-haloalkylsulfanyl having 1 to 9 identical or different halogen atoms; $C_1$-$C_4$-alkylsulfonyl; $C_1$-$C_4$-haloalkylsulfonyl having 1 to 9 identical or different halogen atoms; $C_2$-$C_6$-alkenyl; $C_2$-$C_6$-alkynyl; $C_3$-$C_6$-cycloalkyl; phenyl; tri($C_1$-$C_4$) alkylsilyl; tri($C_1$-$C_4$)alkylsilyl-$C_1$-$C_4$-alkyl.

$R^b$ very particularly preferably represents fluorine, chlorine, bromine; methyl, ethyl, n-propyl, isopropyl, n-, i-, s-, t-butyl, trifluoromethyl, trichloromethyl, difluoromethyl, methoxy, trifluoromethoxy, methylsulfanyl, trifluoromethylsulfanyl, vinyl, allyl, ethynyl, propargyl, cyclopropyl, phenyl, trimethylsilyl.

Unless indicated otherwise, a group or a substituent which is substituted according to the invention is substituted by one or more group selected in the list consisting of halogen; nitro, cyano, $C_1$-$C_{16}$-alkyl; $C_1$-$C_6$-haloalkyl having 1 to 9 identical or different halogen atoms; $C_1$-$C_6$-alkoxy; $C_1$-$C_6$-haloalkoxy having 1 to 9 identical or different halogen atoms; $C_1$-$C_6$-alkylsulfanyl; $C_1$-$C_6$-haloalkylsulfanyl having 1 to 9 identical or different halogen atoms; $C_1$-$C_6$-alkylsulfonyl; $C_1$-$C_6$-haloalkylsulfonyl having 1 to 9 identical or different halogen atoms; $C_2$-$C_{12}$-alkenyl; $C_2$-$C_{12}$-alkynyl; $C_3$-$C_7$-cycloalkyl; phenyl; tri($C_1$-$C_8$)alkylsilyl; tri($C_1$-$C_8$) alkylsilyl-$C_1$-$C_8$-alkyl.

Finally, it has been found that the novel (thio) carboxamides of the formula (I) have very good microbicidal properties and can be used for controlling unwanted microorganisms both in crop protection and in the protection of materials.

The definition $C_1$-$C_{16}$-alkyl comprises the largest range defined here for an alkyl radical. Specifically, this definition comprises the meanings methyl, ethyl, n-, isopropyl, n-, iso-, sec-, tert-butyl, and also in each case all isomeric pentyls, hexyls, heptyls, octyls, nonyls, decyls, undecyls, dodecyls, tridecyls, tetradecyls, pentadecyls, hexadecyls. A preferred range is $C_2$-$C_{12}$-alkyl, such as ethyl and straight-chain or branched propyl, butyl, pentyl, hexyl, heptyl, octyl, nonyl, decyl, undecyl and dodecyl, particularly straight-chain or branched $C_3$-$C_{10}$-alkyl, such as propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-3-methylpropyl, n-heptyl, 1-methylhexyl, 1-ethylpentyl, 2-ethylpentyl, 1-propylbutyl, octyl, 1-methylheptyl, 2-methylheptyl, 1-ethylhexyl, 2-ethylhexyl, 1-propylpentyl, 2-propylpentyl, nonyl, 1-methyloctyl, 2-methyloctyl, 1-ethylheptyl, 2-ethylheptyl, 1-propylhexyl, 2-propylhexyl, decyl, 1-methylnonyl, 2-methylnonyl, 1-ethyloctyl, 2-ethyloctyl, 1-propylheptyl and 2-propylheptyl, in particular propyl, 1-methylethyl, butyl, 1-methylbutyl, 2-methylbutyl, 3-methylbutyl, 1,1-dimethylethyl, 1,2-dimethylbutyl, 1,3-dimethylbutyl, pentyl, 1-methylbutyl, 1-ethylpropyl, hexyl, 3-methylpentyl, heptyl, 1-methylhexyl, 1-ethyl-3-methylbutyl, 1-methylheptyl, 1,2-dimethylhexyl, 1,3-dimethyloctyl, 4-methyloctyl, 1,2,2,3-tetramethylbutyl, 1,3,3-trimethylbutyl, 1,2,3-trimethylbutyl, 1,3-dimethylpentyl, 1,3-dimethylhexyl, 5-methyl-3-hexyl, 2-methyl-4-heptyl, 2,6-dimethyl-4-heptyl and 1-methyl-2-cyclopropylethyl.

Halogen-substituted alkyl represents, for example, chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3-chloro-1-methylbutyl, 2-chloro-1-methylbutyl, 1-chlorobutyl, 3,3-dichloro-1-methylbutyl, 3-chloro-1-methylbutyl, 1-methyl-3-trifluoromethylbutyl, 3-methyl-1-trifluoromethylbutyl.

The definition tri($C_1$-$C_8$)alkylsilyl preferably represents the following radicals: $SiMe_3$, $SiMe_2Et$, $SiMe_2CHMe_2$, $SiMe_2CH_2CHMe_2$, $SiMe_2CH_2CMe_3$, $SiMe_2CMe_3$, $SiMe_2CH_2CH_2Me$.

The definition $C_2$-$C_{16}$-alkenyl comprises the largest range defined here for an alkenyl radical. Specifically, this definition comprises the meanings ethenyl, n-, isopropenyl, n-, iso-, sec-, tert-butenyl, and also in each case all isomeric pentenyls, hexenyls, heptenyls, octenyls, nonenyls, decenyls, undecenyls, dodecenyls, tridecenyls, tetradecenyls, pentadecenyls, hexadecenyls, 1-methyl-1-propenyl, 1-ethyl-1-butenyl, 2,4-dimethyl-1-pentenyl, 2,4-dimethyl-2-pentenyl.

The definition $C_2$-$C_{16}$-alkynyl comprises the largest range defined here for an alkynyl radical. Specifically, this definition comprises the meanings ethynyl, n-, isopropynyl, n-, iso-, sec-, tert-butynyl, and also in each case all isomeric pentynyls, hexynyls, heptynyls, octynyls, nonynyls, decynyls, undecynyls, dodecynyls, tridecynyls, tetradecynyls, pentadecynyls, hexadecynyls.

The definition cycloalkyl comprises monocyclic saturated hydrocarbyl groups having 3 to 8 carbon ring members, such as cyclopropyl, cyclobutyl, cyclopentyl, cyclohexyl, cycloheptyl and cyclooctyl.

The definition aryl comprises unsubstituted or substituted, aromatic, mono-, bi- or tricyclic ring, for example phenyl, naphthyl, anthracenyl (anthryl), phenanthracenyl (phenanthryl).

The definition heterocycle comprises unsubstituted or substituted, unsaturated heterocyclic 5- to 7-membered ring containing up to 4 heteroatoms selected from N, O and S: for example 2-furyl, 3-furyl, 2-thienyl, 3-thienyl, 2-pyrrolyl, 3-pyrrolyl, 1-pyrrolyl, 3-pyrazolyl, 4-pyrazolyl, 5-pyrazolyl, 1-pyrazolyl, 1H-imidazol-2-yl, 1H-imidazol-4-yl, 1H-imidazol-5-yl, 1H-imidazol-1-yl, 2-oxazolyl, 4-oxazolyl, 5-oxazolyl, 2-thiazolyl, 4-thiazolyl, 5-thiazolyl, 3-isoxazolyl, 4-isoxazolyl, 5-isoxazolyl, 3-isothiazolyl, 4-isothiazolyl, 5-isothiazolyl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-3-yl, 1H-1,2,4-triazol-5-yl, 1H-1,2,4-triazol-1-yl, 4H-1,2,4-triazol-3-yl, 4H-1,2,4-triazol-4-yl, 1H-tetrazol-1-yl, 1H-tetrazol-5-yl, 2H-tetrazol-2-yl, 2H-tetrazol-5-yl, 1,2,4-oxadiazol-3-yl, 1,2,4-oxadiazol-5-yl, 1,2,4-thiadiazol-3-yl, 1,2,4-thiadiazol-5-yl, 1,3,4- oxadiazol-2-yl, 1,3,4-thiadiazol-2-yl, 1,2,3-oxadiazol-4-yl, 1,2,3-oxadiazol-5-yl, 1,2,3-thiadiazol-4-yl, 1,2,3-thiadiazol-5-yl, 1,2,5-oxadiazol-3-yl, 1,2,5-thiadiazol-3-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,4-triazin-6-yl.

Optionally substituted radicals may be mono- or polysubstituted, where in the case of polysubstitution, the substituents may be identical or different. Thus, the definition dialkylamino also embraces an amino group which is substituted asymmetrically by alkyl, such as, for example, methylethylamino.

Halogen-substituted radicals, such as, for example, halogenoalkyl, are mono- or polyhalogenated. In the case of polyhalogenation, the halogen atoms may be identical or different. Here, halogen represents fluorine, chlorine, bromine and iodine, in particular fluorine, chlorine and bromine.

However, the general or preferred radical definitions or illustrations given above can also be combined with one another as desired, i.e. including combinations between the respective ranges and preferred ranges. They apply to the end products and, correspondingly, to precursors and intermediates.

The radical definitions and explanations given above in general terms or stated within preferred ranges can, however, also be combined with one another as desired, i.e. including between the particular ranges and preferred ranges. They apply both to the end products and correspondingly to precursors and intermediates. In addition, individual definitions may not apply.

Preference is given to those compounds of the formula (I) in which each of the radicals have the above-mentioned preferred definitions.

Particular preference is given to those compounds of the formula (I) in which each of the radicals have the above-mentioned more preferred definitions.

Very particular preference is given to those compounds of the formula (I) in which each of the radicals have the above-mentioned most preferred definitions.

If appropriate, the compounds according to the invention can be present as mixtures of different possible isomeric forms, in particular of stereoisomers, such as, for example, E and Z, threo and erythro, and also optical isomers, and, if appropriate, also of tautomers. What is claimed are both the E and the Z isomers, and also the threo and erythro, and the optical isomers, any mixtures of these isomers, and the possible tautomeric forms.

If appropriate, the compounds of the present invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions) and to the mixtures of all the possible stereoisomers, in all proportions. The diastereoisomers and/or the optical isomers can be separated according to the methods which are known per se by the man ordinary skilled in the art.

If appropriate, the compounds of the present invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

If appropriate, the compounds of the present invention can also exist in one or more geometric isomer forms depending on the relative position (syn/anti or cis/trans) of the substituents. The invention thus relates equally to all syn/anti (or cis/trans) isomers and to all possible syn/anti (or cis/trans) mixtures, in all proportions. The syn/anti (or cis/trans) isomers can be separated according to general methods, which are known per se by the man ordinary skilled in the art.

Illustration of the Processes and Intermediates Carboxamides of the formula (I-a), wherein T represents oxygen, are obtained when carbonyl halides or acids of formula (II) are reacted with amines of formula (III-a) optionally in the presence of a coupling agent, optionally in the presence of an acid binder and optionally in the presence of a diluent [Process (a)]:

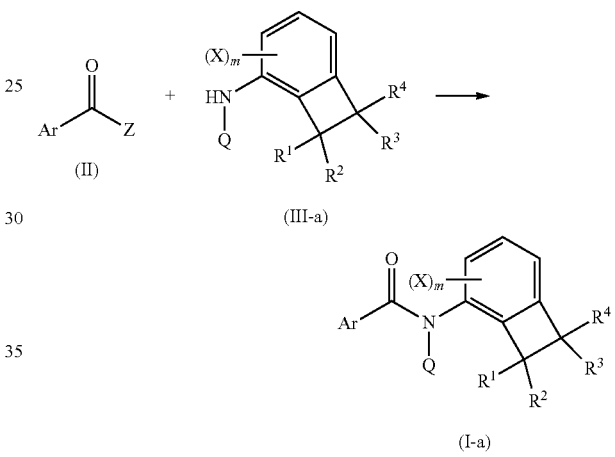

The formula (II) provides a general definition of the carbonyl halides or acids required as starting materials for carrying out the Process (a) according to the invention.

In this formula (II) Ar has generally and preferably those meanings which have already been mentioned for these radicals in connection with the description of the compounds of the formula (I). Z represents halogen, cyano, hydroxyl or an activated hydroxyl group, preferably represents fluorine, chlorine or hydroxyl, particularly preferably chlorine or hydroxyl.

An activated hydroxyl group shall mean that the hydroxyl forms together with the adjacent carbonyl an ester which spontaneously reacts with an amino group. Common activated esters include p-nitrophenyl, pentafluorophenyl, succinimido esters, or phosphorous anhydrides.

The carbonyl halides or acids of the formula (II) can be prepared from commercially available starting material using known procedures (cf. R. C. Larock *Comprehensive organic transformations,* 1989, VCH publishers).

The formula (III-a) provides a general definition of the amines required as starting materials for carrying out the process (a) according to the invention.

In this formula (III-a) Q, X, m, $R^1$, $R^2$, $R^3$ and $R^4$ have generally, preferably, particularly preferably, very particularly preferably those meanings which have already been mentioned for these radicals in connection with the description of the compounds of the formula (I).

Thiocarboxamides of the formula (I-b), wherein T represents sulfur, are obtained when carboxamides of the formula (I-a) are reacted with a thionating agent, optionally in the presence of a diluent, and if appropriate in the presence of a catalytic or stoichiometric or more quantity of an acid binder [Process (b)]:

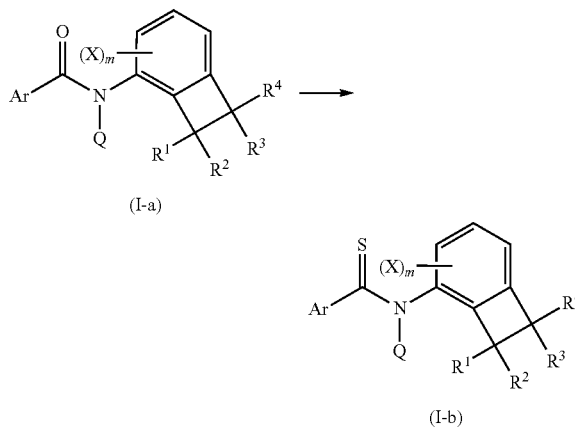

Compounds of formula (III-a) used as starting materials are prepared by reacting bromides of formula (III-b) with compounds according to formula (IV) or with compounds according to formula (V) in the presence of a catalyst, optionally in the presence of an acid binder and/or in the presence of a diluent. An additional step could be necessary to get the free amine (Q equals H) as, for example, a treatment with a suitable acid or hydrogenolysis catalyzed by a metal. [Process (c)]:

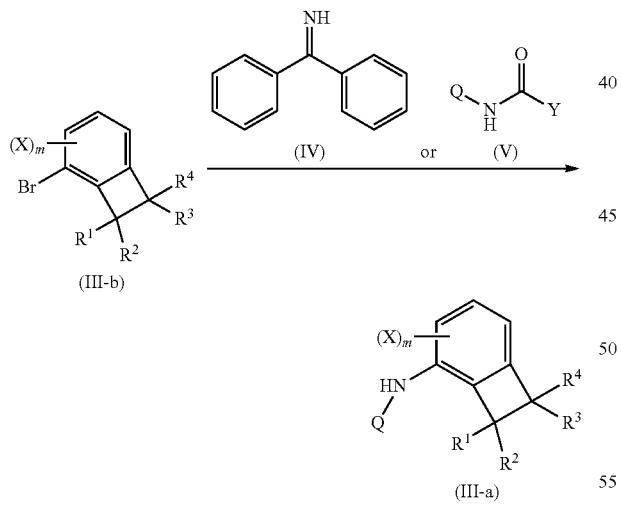

The formula (III-b) provides a general definition of the bromides required as starting materials for carrying out the process (c) according to the invention.

In this formula (III-b) X, m, $R^1$, $R^2$, $R^3$ and $R^4$ have generally, preferably, particularly preferably, very particularly preferably those meanings which have already been mentioned for these radicals in connection with the description of the compounds of the formula (I).

In formula (V) Q has generally, preferably, particularly preferably, very particularly preferably those meanings which have already been mentioned for these radicals in connection with the description of the compounds of the formula (I), Y represents hydrogen, $C_1$-$C_6$ alkyl, $C_1$-$C_6$ alkyloxy, phenoxy, benzyloxy.

Compounds of formula (III-b) used as starting materials are prepared by cyclizing compounds of formula (VV) in the presence of a mediating agent, a brominating agent and in the presence of a diluent (adaptation of Bailey, W. F. *Tetrahedron letters,* 1999, 40, 6899) [Process (d)]:

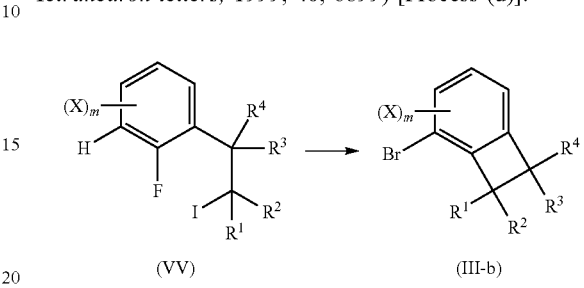

The formula (VV) provides a general definition of the iodides required as starting materials for carrying out the Process (d) according to the invention.

In this formula (VV) X, m, $R^1$, $R^2$, $R^3$ and $R^4$ have generally, preferably, particularly preferably, very particularly preferably those meanings which have already been mentioned for these radicals in connection with the description of the compounds of the formula (I).

Compounds of formula (VV) are commercially available or can be prepared according to known methods (Bailey, W. F. *Tetrahedron letters,* 1999, 40, 6899).

Compounds of formula (III-b), especially when $R^1$ and $R^2$ represent $C_1$-$C_{16}$-alkoxy, are prepared by reacting compounds of formula (VI) with compounds of formula (VII) in the presence of a base and in the presence of a diluent [Process (e)]:

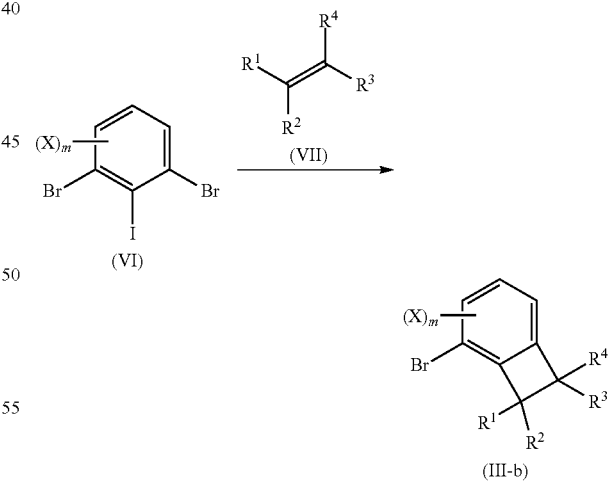

The formula (VI) provides a general definition of the iodides required as starting materials for carrying out the Process (e) according to the invention.

In this formula (VI), X and m have generally, preferably, particularly preferably, very particularly preferably those meanings which have already been mentioned for these radicals in connection with the description of the compounds of the formula (I).

In formula (VII), $R^1$, $R^2$, $R^3$ and $R^4$ have generally, preferably, particularly preferably, very particularly preferably those meanings which have already been mentioned for these radicals in connection with the description of the compounds of formula (I).

Compounds of formula (VI) and compounds of formula (VII) are commercially available.

Alternatively, compounds of formula (III-c), ie compounds of formula (III-a) wherein Q represents hydrogen, are prepared by reacting compounds of formula (III-d) with an azide source, optionally in the presence of an activating agent, optionally in the presence of a diluent, optionally in the presence of an acid binder (process f):

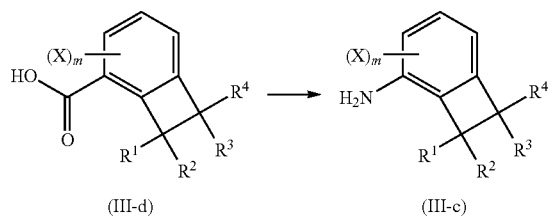

(III-d)     (III-c)

An additional step could be necessary to liberate the amine under its unprotected form such as, for example, a treatment with a suitable acid or hydrogenolysis catalyzed by a metal.

The formula (III-d) provides a general definition of the carboxylic acids required as starting materials for carrying out the process (f) according to the invention.

In this formula (III-d) X, m, $R^1$, $R^2$, $R^3$ and $R^4$ have generally, preferably, particularly preferably, very particularly preferably those meanings which have already been mentioned for these radicals in connection with the description of the compounds of the formula (I).

Compounds of formula (III-d) are prepared by oxidizing compounds of formula (III-e) using classical procedures known from literature (R. C. Larock *Comprehensive organic transformations*, 1989, VCH publishers), optionally in the presence of a diluent (process g):

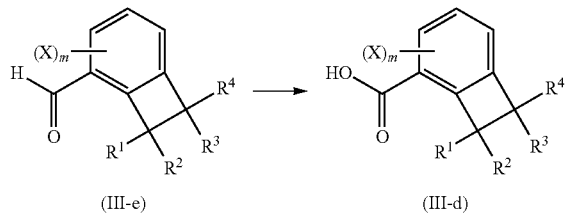

(III-e)     (III-d)

The formula (III-e) provides a general definition of the aldehydes required as starting materials for carrying out the process (g) according to the invention.

In this formula (III-e) X, m, $R^1$, $R^2$, $R^3$ and $R^4$ have generally, preferably, particularly preferably, very particularly preferably those meanings which have already been mentioned for these radicals in connection with the description of the compounds of the formula (I).

Compounds of formula (III-e) used as starting materials are prepared by cyclizing compounds of formula (VV) in the presence of a mediating agent, DMF and in the presence of a diluent (adaptation of Bailey, W. F. *Tetrahedron letters*, 1999, 40, 6899) [Process (h)]:

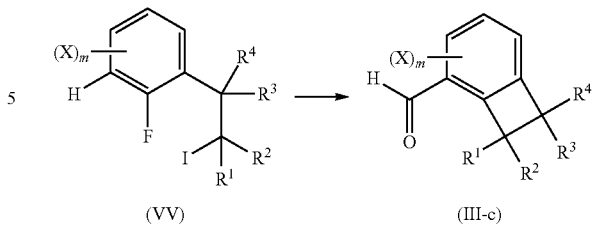

(VV)     (III-c)

Suitable diluents for carrying out the processes (a), (b), (c), (d), (e), (f), (g) and (h) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decaline; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisol; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; their mixtures with water or pure water.

Suitable acid binders for carrying out the processes (a), (b), (c) and (f) according to the invention can be inorganic and organic bases which are customary for such reactions. Preference is given to using alkaline earth metal, alkali metal hydride, alkali metal hydroxides or alkali metal alkoxides, such as sodium hydroxide, sodium hydride, calcium hydroxide, potassium hydroxide, potassium tert-butoxide or other ammonium hydroxide, alkali metal carbonates, such as sodium carbonate, potassium carbonate, potassium bicarbonate, sodium bicarbonate, cesium carbonate, alkali metal or alkaline earth metal acetates, such as sodium acetate, potassium acetate, calcium acetate, and also tertiary amines, such as trimethylamine, triethylamine, diisopropylethylamine, tributylamine, N,N-dimethylaniline, pyridine, N-methylpiperidine, N,N-dimethylaminopyridine, 1,4-diazabicyclo[2.2.2]octane (DAB-CO), 1,5-diazabicyclo[4.3.0]non-5-ene (DBN) or 1,8-diazabicyclo[5.4.0]undec-7-ene (DBU).

The Process (a) according to the invention is, if appropriate, carried out in the presence of a suitable coupling agent when $X^3$ represents hydroxyl. Suitable coupling agents are all customary carbonyl activators. These preferably include N-[3-(dimethylamino)propyl]-N'-ethyl-carbodiimide-hydrochloride, N,N'-di-sec-butylcarbodiimide, N,N'-dicyclohexylcarbodiimide, N,N'-diisopropylcarbodiimide, 1-(3-(dimethylamino)propyl)-3-ethylcarbodiimide methiodide, 2-bromo-3-ethyl-4-methylthiazolium tetrafluoroborate, N,N-bis[2-oxo-3-oxazolidinyl]-phosphorodiamidic chloride, chlorotripyrrolidinophosphonium hexafluorophosphate, bromtripyrrolidinophosphonium hexafluorophosphate, O-(1H-benzotriazol-1-yloxy)tris(dimethylamino)phosphonium hexafluorophosphate, O-(1H-benzotriazol-1-yl)-N,N,N',N'-tetramethyluronium hexafluorophosphate, O-(1H-benzotriazol-1-yl)-N,N,N',N'-bis (tetramethylene)uronium hexafluorophosphate, O-(1H-benzotriazol-1-yl)-N,N,N',N'-bis(tetramethylene)uronium tetrafluoroborate, N,N,N',N'-bis(tetramethylene)chlorouronium tetrafluoroborate, O-(7-azabenzotriazol-1-yl)-N,N,N, N-tetramethyluronium hexafluorophosphate and 1-hydroxybenzotriazole. These reagents can be employed separately, but also in combination.

When carrying out the Process (a) according to the invention, the reaction temperatures can be varied within a relatively wide range. In general, the process is carried out at temperatures of from 0° C. to 150° C., preferably at temperatures of from 20° C. to 110° C.

For carrying out the Process (a) according to the invention for preparing the compounds of the formula (I-a) in general from 0.2 to 5 mol, preferably from 0.5 to 2 mol, of amine of the formula (III-a) are employed per mole of the carbonyl halide or acid of the formula (II). Work-up is carried out by customary methods.

For carrying out the Process (b) according to the invention for preparing the compounds of the formula (I-b) starting amide derivatives of formula (I-a) can be prepared according to Process (a).

Suitable thionating agents for carrying out Process (b) according to the invention can be sulfur (S), sulfhydric acid ($H_2S$), sodium sulfide ($Na_2S$), sodium hydrosulfide (NaHS), boron trisulfide ($B_2S_3$), bis(diethylaluminium) sulfide (($AlEt_2)_2S$), ammonium sulfide (($NH_4)_2S$), phosphorous pentasulfide ($P_2S_5$), Lawesson's reagent (2,4-bis(4-methoxyphenyl)-1,2,3,4-dithiadiphosphetane 2,4-disulfide) or a polymer-supported thionating reagent such as described in J. Chem. Soc., Perkin 1 2001, 358.

Process (c) is performed in the presence of a catalyst, optionally in the presence of an acid binder, optionally in the presence of a diluent and followed by treatment with a suitable acid. Suitable acids for this propose are chosen amongst usual Brønsted acids such as for example HCl, $H_2SO_4$, $KHSO_4$, AcOH, trifluoroacetic acid, p-toluenesulfonic acid, camphorsulfonic acid, triethanolamine-HCl, Pyridine HCl.

Suitable catalysts for carrying out processes (c) according to the invention may be chosen from metal salt or complex. Suitable metal derivatives for this purpose are based on palladium or copper. Suitable metal salts or complexes for this purpose are palladium chloride, palladium acetate, tetrakis(triphenylphosphine)palladium, bis(triphenylphosphine)palladium dichloride or 1,1'-bis(diphenylphosphino)ferrocenepalladium(III) chloride, copper iodide, copper bromide, copper thiophene carboxylate, copper trifluoromethane sulfonate, copper (I) oxide It is also possible to generate a palladium complex in the reaction mixture by separate addition to the reaction of a palladium salt and a ligand or salt, such as a phosphine, for example triethylphosphine, tri-tert-butylphosphine, tricyclohexylphosphine, 2-(dicyclohexylphosphine)biphenyl, 2-(di-tert-butylphosphin)biphenyl, 2-(dicyclohexylphosphine)-2'-(N,N-dimethylamino)-biphenyl, triphenylphosphine, tris-(o-tolyl)phosphine, sodium 3-(diphenylphosphino)benzolsulfonate, tris-2-(methoxyphenyl)phosphine, 2,2'-bis-(diphenylphosphine)-1,1'-binaphthyl, 1,4-bis-(diphenylphosphine)butane, 1,2-bis-(diphenylphosphine)ethane, 1,4-bis-(dicyclohexylphosphine)butane, 1,2-bis-(dicyclohexylphosphine)ethane, 2-(dicyclohexylphosphine)-2'-(N,N-dimethylamino)-biphenyl, bis(diphenylphosphino)ferrocene, tris-(2,4-tert-butylphenyl)-phosphite, (R)-(−)-1-[(S)-2-(diphenylphosphino)ferrocenyl]ethyldi-tert-butylphosphine, (S)-(+)-1-[(R)-2-(diphenylphosphino)ferrocenyl]-ethyldicyclohexylphosphine, (R)-(−)-1-[(S)-2-(diphenylphosphino)ferrocenyl] ethyldicyclohexylphosphine, (S)-(+)-1-[(R)-2-(diphenylphosphino)ferrocenyl]ethyldi-t-butylphosphine or 1,3-bis(2,4,6-trimethylphenyl)imidazolium chloride.

It is also possible to generate a copper complex in the reaction mixture by separate addition to the reaction of a copper salt and a ligand or salt, such as a diamine for example cyclohexyl 1,2-diamine, N,N'-dimethylethylene diamine, cyclohexyl N,N'-dimethylamine.

It is also advantageous to choose the appropriate catalyst and/or ligand from commercial catalogues such as "Metal Catalysts for Organic Synthesis" by Strem Chemicals or "Phosphorous Ligands and Compounds" by Strem Chemicals.

When carrying out the Process (c) according to the invention, the reaction temperatures can be varied within a relatively wide range. In general, the process is carried out at temperatures of from 0° C. to 150° C., preferably at temperatures of from 20° C. to 110° C.

For carrying out the Process (c) according to the invention for preparing the compounds of the formula (III-a) in general from 0.2 to 5 mol, preferably from 0.5 to 2 mol, of compound of the formula (IV) are employed per mole of bromides of the formula (III-b). Work-up is carried out by customary methods.

Suitable mediating agents for carrying out the processes (d), (e) and (h) according to the invention can be alkyl lithium or alkyl magnesium reagents such as, for example, n-butyllithium, sec-butyllithium, tert-butyllithium, methyl magnesium chloride, ethyl magnesium chloride or isopropyl magnesium chloride.

Suitable brominating agents for carrying out the Process (d) according to the invention may be chosen from 1,2-dibromoethane, bromine or N-bromosuccinimide.

The Process (f) according to the invention is, if appropriate, carried out in the presence of a suitable coupling agent. Suitable coupling agents are all customary carbonyl activators When carrying out the processes (d), (e) and (h) according to the invention, the reaction temperatures can be varied within a relatively wide range. In general, the process is carried out at temperatures of from −100° C. to 0° C., preferably at temperatures of from −78° C. to −45° C.

The Processes (a), (b), (c), (d), (e), (f), (g) and (h) are generally carried out under atmospheric pressure. However, it is also possible to operate under elevated or reduced pressure—in general between 0.1 bar and 100 bar.

Composition/Formulation

The present invention further relates to a crop protection composition for controlling unwanted microorganisms, especially unwanted fungi and bacteria, comprising an effective and non-phytotoxic amount of the inventive active ingredients. These are preferably fungicidal compositions which comprise agriculturally suitable auxiliaries, solvents, carriers, surfactants or extenders.

In the context of the present invention, "control of harmful microorganisms" means a reduction in infestation by harmful microorganisms, compared with the untreated plant measured as fungicidal efficacy, preferably a reduction by 25-50%, compared with the untreated plant (100%), more preferably a reduction by 40-79%, compared with the untreated plant (100%); even more preferably, the infection by harmful microorganisms is entirely suppressed (by 70-100%). The control may be curative, i.e. for treatment of already infected plants, or protective, for protection of plants which have not yet been infected.

An "effective but non-phytotoxic amount" means an amount of the inventive composition which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on several factors, for example on the fungus to be controlled, the plant, the climatic conditions and the ingredients of the inventive compositions.

Suitable organic solvents include all polar and non-polar organic solvents usually employed for formulation purposes. Preferable the solvents are selected from ketones, e.g. methyl-isobutyl-ketone and cyclohexanone, amides, e.g. dimethyl formamide and alkanecarboxylic acid amides, e.g. N,N-dimethyl decaneamide and N,N-dimethyl octanamide, furthermore cyclic solvents, e.g. N-methyl-pyrrolidone, N-octyl-pyrrolidone, N-dodecyl-pyrrolidone, N-octyl-caprolactame, N-dodecyl-caprolactame and butyrolactone, furthermore strong polar solvents, e.g. dimethylsulfoxide, and aromatic hydrocarbons, e.g. xylol, Solvesso™, mineral oils, e.g. white spirit, petroleum, alkyl benzenes and spindle oil, also esters, e.g. propyleneglycol-monomethylether acetate, adipic acid dibutylester, acetic acid hexylester, acetic acid heptylester, citric acid tri-n-butylester and phthalic acid di-n-butylester, and also alcohols, e.g. benzyl alcohol and 1-methoxy-2-propanol.

According to the invention, a carrier is a natural or synthetic, organic or inorganic substance with which the active ingredients are mixed or combined for better applicability, in particular for application to plants or plant parts or seed. The carrier, which may be solid or liquid, is generally inert and should be suitable for use in agriculture.

Useful solid or liquid carriers include: for example ammonium salts and natural rock dusts, such as kaolins, clays, talc, chalk, quartz, attapulgite, montmorillonite or diatomaceous earth, and synthetic rock dusts, such as finely divided silica, alumina and natural or synthetic silicates, resins, waxes, solid fertilizers, water, alcohols, especially butanol, organic solvents, mineral and vegetable oils, and derivatives thereof. Mixtures of such carriers can likewise be used.

Suitable solid filler and carrier include inorganic particles, e.g. carbonates, silikates, sulphates and oxides with an average particle size of between 0.005 and 20 µm, preferably of between 0.02 to 10 µm, for example ammonium sulphate, ammonium phosphate, urea, calcium carbonate, calcium sulphate, magnesium sulphate, magnesium oxide, aluminium oxide, silicium dioxide, so-called fine-particle silica, silica gels, natural or synthetic silicates, and alumosilicates and plant products like cereal flour, wood powder/sawdust and cellulose powder.

Useful solid carriers for granules include: for example crushed and fractionated natural rocks such as calcite, marble, pumice, sepiolite, dolomite, and synthetic granules of inorganic and organic meals, and also granules of organic material such as sawdust, coconut shells, maize cobs and tobacco stalks.

Useful liquefied gaseous extenders or carriers are those liquids which are gaseous at standard temperature and under standard pressure, for example aerosol propellants such as halohydrocarbons, and also butane, propane, nitrogen and carbon dioxide.

In the formulations, it is possible to use tackifiers such as carboxymethylcellulose, and natural and synthetic polymers in the form of powders, granules or latices, such as gum arabic, polyvinyl alcohol and polyvinyl acetate, or else natural phospholipids, such as cephalins and lecithins, and synthetic phospholipids. Further additives may be mineral and vegetable oils.

If the extender used is water, it is also possible to employ, for example, organic solvents as auxiliary solvents. Useful liquid solvents are essentially: aromatics such as xylene, toluene or alkylnaphthalenes, chlorinated aromatics and chlorinated aliphatic hydrocarbons such as chlorobenzenes, chloroethylenes or dichloromethane, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

Suitable surfactants (adjuvants, emulsifiers, dispersants, protective colloids, wetting agent and adhesive) include all common ionic and non-ionic substances, for example ethoxylated nonylphenols, polyalkylene glycolether of linear or branched alcohols, reaction products of alkyl phenols with ethylene oxide and/or propylene oxide, reaction products of fatty acid amines with ethylene oxide and/or propylene oxide, furthermore fattic acid esters, alkyl sulfonates, alkyl sulphates, alkyl ethersulphates, alkyl etherphosphates, arylsulphate, ethoxylated arylalkylphenols, e.g. tristyrylphenol-ethoxylates, furthermore ethoxylated and propoxylated arylalkylphenols like sulphated or phosphated arylalkylphenol-ethoxylates and -ethoxy- and -propoxylates. Further examples are natural and synthetic, water soluble polymers, e.g. lignosulphonates, gelatine, gum arabic, phospholipides, starch, hydrophobic modified starch and cellulose derivatives, in particular cellulose ester and cellulose ether, further polyvinyl alcohol, polyvinyl acetate, polyvinyl pyrrolidone, polyacylic acid, polymethacrylic acid and co-polymerisates of (meth)acrylic acid and (meth)acrylic acid esters, and further co-polymerisates of methacrylic acid and methacrylic acid esters which are neutralized with alkali-metal hydroxide and also condensation products of optionally substituted naphthalene sulfonic acid salts with formaldehyde. The presence of a surfactant is necessary if one of the active ingredients and/or one of the inert carriers is insoluble in water and when application is effected in water. The proportion of surfactants is between 5 and 40 percent by weight of the inventive composition.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Antifoams which may be present in the formulations include e.g. silicone emulsions, longchain alcohols, fatty acids and their salts as well as fluoroorganic substances and mixtures thereof.

Examples of thickeners are polysaccharides, e.g. xanthan gum or veegum, silicates, e.g. attapulgite, bentonite as well as fine-particle silica.

If appropriate, it is also possible for other additional components to be present, for example protective colloids, binders, adhesives, thickeners, thixotropic substances, penetrants, stabilizers, sequestrants, complexing agents. In general, the active ingredients can be combined with any solid or liquid additive commonly used for formulation purposes.

The inventive active ingredients or compositions can be used as such or, depending on their particular physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, gas (under pressure), gas generating product, foams, pastes, pesticide coated seed, suspension concentrates, suspoemulsion concentrates, soluble concentrates, suspensions, wettable powders, soluble powders, dusts and granules, water-soluble and water-dispersible granules or tablets, water-soluble and water-dispersible powders for the treatment of seed, wettable powders, natural products and synthetic substances impregnated with active ingredient, and also microencapsulations in polymeric substances and in coating materials for seed, and also ULV cold-fogging and warm-fogging formulations.

The inventive compositions include not only formulations which are already ready for use and can be applied with a suitable apparatus to the plant or the seed, but also commercial concentrates which have to be diluted with water prior to use. Customary applications are for example dilution in water and subsequent spraying of the resulting spray liquor, application after dilution in oil, direct application without dilution, seed treatment or soil application of granules.

The inventive compositions and formulations generally contain between 0.05 and 99% by weight, 0.01 and 98% by weight, preferably between 0.1 and 95% by weight, more preferably between 0.5 and 90% of active ingredient, most preferably between 10 and 70% by weight. For special applications, e.g. for protection of wood and derived timber products the inventive compositions and formulations generally contain between 0.0001 and 95% by weight, preferably 0.001 to 60% by weight of active ingredient.

The contents of active ingredient in the application forms prepared from the commercial formulations may vary in a broad range. The concentration of the active ingredients in the application forms is generally between 0.000001 to 95% by weight, preferably between 0.0001 and 2% by weight.

The formulations mentioned can be prepared in a manner known per se, for example by mixing the active ingredients with at least one customary extender, solvent or diluent, adjuvant, emulsifier, dispersant, and/or binder or fixative, wetting agent, water repellent, if appropriate desiccants and UV stabilizers and, if appropriate, dyes and pigments, antifoams, preservatives, inorganic and organic thickeners, adhesives, gibberellins and also further processing auxiliaries and also water. Depending on the formulation type to be prepared further processing steps are necessary, e.g. wet grinding, dry grinding and granulation.

The inventive active ingredients may be present as such or in their (commercial) formulations and in the use forms prepared from these formulations as a mixture with other (known) active ingredients.

The inventive treatment of the plants and plant parts with the active ingredients or compositions is effected directly or by action on their surroundings, habitat or storage space by the customary treatment methods, for example by dipping, spraying, atomizing, irrigating, evaporating, dusting, fogging, broadcasting, foaming, painting, spreading-on, watering (drenching), drip irrigating and, in the case of propagation material, especially in the case of seeds, also by dry seed treatment, wet seed treatment, slurry treatment, incrustation, coating with one or more coats, etc. It is also possible to deploy the active ingredients by the ultra-low volume method or to inject the active ingredient preparation or the active ingredient itself into the soil.

Plant/Crop Protection

The inventive active ingredients or compositions have potent microbicidal activity and can be used for control of unwanted microorganisms, such as fungi and bacteria, in crop protection and in the protection of materials.

The invention also relates to a method for controlling unwanted microorganisms, characterized in that the inventive active ingredients are applied to the phytopathogenic fungi, phytopathogenic bacteria and/or their habitat.

Fungicides can be used in crop protection for control of phytopathogenic fungi. They are characterized by an outstanding efficacy against a broad spectrum of phytopathogenic fungi, including soilborne pathogens, which are in particular members of the classes Plasmodiophoromycetes, Peronosporomycetes (Syn. Oomycetes), Chytridiomycetes, Zygomycetes, Ascomycetes, Basidiomycetes and Deuteromycetes (Syn. Fungi imperfecti). Some fungicides are systemically active and can be used in plant protection as foliar, seed dressing or soil fungicide. Furthermore, they are suitable for combating fungi, which inter alia infest wood or roots of plant.

Bactericides can be used in crop protection for control of Pseudomonadaceae, Rhizobiaceae, Enterobacteriaceae, Corynebacteriaceae and Streptomycetaceae.

Non-limiting examples of pathogens of fungal diseases which can be treated in accordance with the invention include:

diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*;

diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* and *Phakopsora meibomiae*; *Puccinia* species, for example *Puccinia recondite, P. triticina, P. graminis* or *P. striiformis*; *Uromyces* species, for example *Uromyces appendiculatus*;

diseases caused by pathogens from the group of the Oomycetes, for example *Albugo* species, for example *Algubo candida*; *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; *Pythium* species, for example *Pythium ultimum*;

leaf blotch diseases and leaf wilt diseases caused, for example, by *Alternaria* species, for example *Alternaria solani*; *Cercospora* species, for example *Cercospora beticola*; *Cladiosporium* species, for example *Cladiosporium cucumerinum*; *Cochliobolus* species, for example *Cochliobolus sativus* (conidia form: Drechslera, Syn: Helminthosporium), *Cochliobolus miyabeanus*; *Colletotrichum* species, for example *Colletotrichum lindemuthianum*; *Cycloconium* species, for example *Cycloconium oleaginum*; *Diaporthe* species, for example *Diaporthe citri*; *Elsinoe* species, for example *Elsinoe fawcettii*; *Gloeosporium* species, for example *Gloeosporium laeticolor*; *Glomerella* species, for example *Glomerella cingulata*; *Guignardia* species, for example *Guignardia bidwelli*; *Leptosphaeria* species, for example *Leptosphaeria maculans, Leptosphaeria nodorum*; *Magnaporthe* species, for example *Magnaporthe grisea*; *Microdochium* species, for example *Microdochium nivale*; *Mycosphaerella* species, for example *Mycosphaerella graminicola, M. arachidicola* and *M. fijiensis*; *Phaeosphaeria* species, for example *Phaeosphaeria nodorum*;

*Pyrenophora* species, for example *Pyrenophora teres, Pyrenophora tritici repentis*; *Ramularia* species, for example *Ramularia collo-cygni, Ramularia areola*; *Rhynchosporium* species, for example *Rhynchosporium secalis*; *Septoria* species, for example *Septoria apii, Septoria lycopersii*; *Typhula* species, for example *Typhula incarnata*; *Venturia* species, for example *Venturia inaequalis*;

root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Rhizoctonia* species, such as, for example *Rhizoctonia solani*; *Sarocladium* diseases caused for example by *Sarocladium oryzae*; *Sclerotium* diseases caused for example by *Sclerotium oryzae*; *Tapesia* species, for example *Tapesia acuformis*; *Thielaviopsis* species, for example *Thielaviopsis basicola*;

ear and panicle diseases (including corn cobs) caused, for example, by *Alternaria* species, for example *Alternaria* spp.; *Aspergillus* species, for example *Aspergillus flavus*; *Cladosporium* species, for example *Cladosporium cladosporioides*; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; *Septoria* species, for example *Septoria nodorum*;

diseases caused by smut fungi, for example *Sphacelotheca* species, for example *Sphacelotheca reiliana*; *Tilletia* species, for example *Tilletia caries, T. controversa*; *Urocystis* species, for example *Urocystis occulta*; *Ustilago* species, for example *Ustilago nuda, U. nuda tritici*;

fruit rot caused, for example, by *Aspergillus* species, for example *Aspergillus flavus*; *Botrytis* species, for example *Botrytis cinerea*; *Penicillium* species, for example *Penicillium expansum* and *P. purpurogenum*; *Sclerotinia* species, for example *Sclerotinia sclerotiorum*; *Verticilium* species, for example *Verticilium alboatrum*;

seed and soilborne decay, mould, wilt, rot and damping-off diseases caused, for example, by *Alternaria* species, caused for example by *Alternaria brassicicola*; *Aphanomyces* species, caused for example by *Aphanomyces euteiches*; *Ascochyta* species, caused for example by *Ascochyta lentis*; *Aspergillus* species, caused for example by *Aspergillus flavus*; *Cladosporium* species, caused for example by *Cladosporium herbarum*; *Cochliobolus* species, caused for example by *Cochliobolus sativus*; (Conidia form: Drechslera, Bipolaris Syn: Helminthosporium); *Colletotrichum* species, caused for example by *Colletotrichum coccodes*; *Fusarium* species, caused for example by *Fusarium culmorum*; *Gibberella* species, caused for example by *Gibberella zeae*; *Macrophomina* species, caused for example by *Macrophomina phaseolina*; *Monographella* species, caused for example by *Monographella nivalis*; *Penicillium* species, caused for example by *Penicillium expansum*; *Phoma* species, caused for example by *Phoma lingam*; *Phomopsis* species, caused for example by *Phomopsis sojae*; *Phytophthora* species, caused for example by *Phytophthora cactorum*; *Pyrenophora* species, caused for example by *Pyrenophora graminea*; *Pyricularia* species, caused for example by *Pyricularia oryzae*; *Pythium* species, caused for example by *Pythium ultimum*; *Rhizoctonia* species, caused for example by *Rhizoctonia solani*; *Rhizopus* species, caused for example by *Rhizopus oryzae*; *Sclerotium* species, caused for example by *Sclerotium rolfsii*; *Septoria* species, caused for example by *Septoria nodorum*; *Typhula* species, caused for example by *Typhula incarnata*; *Verticillium* species, caused for example by *Verticillium dahliae*;

cancers, galls and witches' broom caused, for example, by *Nectria* species, for example *Nectria galligena*;

wilt diseases caused, for example, by *Monilinia* species, for example *Monilinia laxa*;

leaf blister or leaf curl diseases caused, for example, by *Exobasidium* species, for example *Exobasidium vexans*; *Taphrina* species, for example *Taphrina deformans*;

decline diseases of wooden plants caused, for example, by Esca disease, caused for example by *Phaemoniella clamydospora, Phaeoacremonium aleophilum* and *Fomitiporia mediterranea*; Eutypa dyeback, caused for example by *Eutypa lata*; Ganoderma diseases caused for example by *Ganoderma boninense*; Rigidoporus diseases caused for example by *Rigidoporus lignosus*;

diseases of flowers and seeds caused, for example, by *Botrytis* species, for example *Botrytis cinerea*;

diseases of plant tubers caused, for example, by *Rhizoctonia* species, for example *Rhizoctonia solani*; *Helminthosporium* species, for example *Helminthosporium solani*;

Club root caused, for example, by *Plasmodiophora* species, for example *Plasmodiophora brassicae*;

diseases caused by bacterial pathogens, for example *Xanthomonas* species, for example *Xanthomonas campestris* pv. *oryzae*; *Pseudomonas* species, for example *Pseudomonas syringae* pv. *lachrymans*; *Erwinia* species, for example *Erwinia amylovora*.

The following diseases of soya beans can be controlled with preference:

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllosticta leaf spot (*Phyllosticta sojaecola*), pod and stem blight (*Phomopsis sojae*), powdery mildew (*Microsphaera diffisa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The inventive fungicidal compositions can be used for curative or protective/preventive control of phytopathogenic fungi. The invention therefore also relates to curative and protective methods for controlling phytopathogenic fungi by the use of the inventive active ingredients or compositions, which are applied to the seed, the plant or plant parts, the fruit or the soil in which the plants grow.

The fact that the active ingredients are well tolerated by plants at the concentrations required for controlling plant diseases allows the treatment of above-ground parts of plants, of propagation stock and seeds, and of the soil.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

The inventive active ingredients, when they are well tolerated by plants, have favourable homeotherm toxicity and are well tolerated by the environment, are suitable for protecting plants and plant organs, for enhancing harvest yields, for improving the quality of the harvested material. They can preferably be used as crop protection compositions. They are active against normally sensitive and resistant species and against all or some stages of development.

Plants which can be treated in accordance with the invention include the following main crop plants: maize, soya bean, alfalfa, cotton, sunflower, *Brassica* oil seeds such as *Brassica napus* (e.g. canola, rapeseed), *Brassica rapa, B. juncea* (e.g. (field) mustard) and *Brassica carinata, Arecaceae* sp. (e.g. oilpalm, coconut), rice, wheat, sugar beet, sugar cane, oats, rye, barley, millet and sorghum, triticale, flax, nuts, grapes and vine and various fruit and vegetables from various botanic taxa, e.g. *Rosaceae* sp. (e.g. pome fruits such as apples and pears, but also stone fruits such as apricots, cherries, almonds, plums and peaches, and berry fruits such as strawberries, raspberries, red and black currant and gooseberry), *Ribesioidae* sp., *Juglandaceae* sp., *Betulaceae* sp., *Anacardiaceae* sp., *Fagaceae* sp., *Moraceae* sp., *Oleaceae* sp. (e.g. olive tree), *Actinidaceae* sp., *Lauraceae* sp. (e.g. avocado, cinnamon, camphor), *Musaceae* sp. (e.g. banana trees and plantations), *Rubiaceae* sp. (e.g. coffee), *Theaceae* sp. (e.g. tea), *Sterculiceae* sp., *Rutaceae* sp. (e.g. lemons, oranges, mandarins and grapefruit); *Solanaceae* sp. (e.g. tomatoes, potatoes, peppers, capsicum, aubergines, tobacco), *Liliaceae* sp., *Compositae* sp. (e.g. lettuce, artichokes and chicory—including root chicory, endive or common chicory), *Umbelliferae* sp. (e.g. carrots, parsley, celery and celeriac), *Cucurbitaceae* sp. (e.g. cucumbers—including gherkins, pumpkins, watermelons, calabashes and melons), *Alliaceae* sp. (e.g. leeks and onions), *Cruciferae* sp. (e.g. white cabbage, red cabbage, broccoli, cauliflower, Brussels sprouts, pak choi, kohlrabi, radishes, horseradish, cress and chinese cabbage), *Leguminosae* sp. (e.g. peanuts, peas, lentils and beans—e.g. common beans and broad beans), *Chenopodiaceae* sp. (e.g. Swiss chard, fodder beet, spinach, beetroot), *Linaceae* sp. (e.g. hemp), *Cannabeacea* sp. (e.g. cannabis), *Malvaceae* sp. (e.g. okra, cocoa), *Papaveraceae* (e.g. poppy), *Asparagaceae* (e.g. asparagus); useful plants and ornamental plants in the garden and woods including turf, lawn, grass and *Stevia rebaudiana*; and in each case genetically modified types of these plants.

Seed Treatment

The invention further comprises a method for treating seed.

The invention further relates to seed which has been treated by one of the methods described in the previous paragraph. The inventive seeds are employed in methods for the protection of seed from unwanted microorganisms. In these methods, seed treated with at least one inventive active ingredient is used.

The inventive active ingredients or compositions are also suitable for treating seed. A large part of the damage to crop plants caused by harmful organisms is triggered by the infection of the seed during storage or after sowing, and also during and after germination of the plant. This phase is particularly critical since the roots and shoots of the growing plant are particularly sensitive, and even minor damage may result in the death of the plant. There is therefore a great interest in protecting the seed and the germinating plant by using appropriate compositions.

The control of phytopathogenic fungi by treating the seed of plants has been known for a long time and is the subject of constant improvements. However, the treatment of seed entails a series of problems which cannot always be solved in a satisfactory manner. For instance, it is desirable to develop methods for protecting the seed and the germinating plant, which dispense with, or at least significantly reduce, the additional deployment of crop protection compositions after planting or after emergence of the plants. It is also desirable to optimize the amount of the active ingredient used so as to provide the best possible protection for the seed and the germinating plant from attack by phytopathogenic fungi, but without damaging the plant itself by the active ingredient employed. In particular, methods for the treatment of seed should also take account of the intrinsic fungicidal properties of transgenic plants in order to achieve optimal protection of the seed and the germinating plant with a minimum expenditure of crop protection compositions.

The present invention therefore also relates to a method for protection of seed and germinating plants from attack by phytopathogenic fungi, by treating the seed with an inventive composition. The invention likewise relates to the use of the inventive compositions for treatment of seed to protect the seed and the germinating plant from phytopathogenic fungi. The invention further relates to seed which has been treated with an inventive composition for protection from phytopathogenic fungi.

The control of phytopathogenic fungi which damage plants post-emergence is effected primarily by treating the soil and the above-ground parts of plants with crop protection compositions. Owing to the concerns regarding a possible influence of the crop protection compositions on the environment and the health of humans and animals, there are efforts to reduce the amount of active ingredients deployed.

One of the advantages of the present invention is that the particular systemic properties of the inventive active ingredients and compositions mean that treatment of the seed with these active ingredients and compositions not only protects the seed itself, but also the resulting plants after emergence, from phytopathogenic fungi. In this way, the immediate treatment of the crop at the time of sowing or shortly thereafter can be dispensed with.

It is likewise considered to be advantageous that the inventive active ingredients or compositions can especially also be used with transgenic seed, in which case the plant growing from this seed is capable of expressing a protein which acts against pests. By virtue of the treatment of such seed with the inventive active ingredients or compositions, merely the expression of the protein, for example an insecticidal protein, can control certain pests. Surprisingly, a further synergistic effect can be observed in this case, which additionally increases the effectiveness for protection against attack by pests.

The inventive compositions are suitable for protecting seed of any plant variety which is used in agriculture, in greenhouses, in forests or in horticulture and viticulture. In particular, this is the seed of cereals (such as wheat, barley, rye, triticale, sorghum/millet and oats), maize, cotton, soya beans, rice, potatoes, sunflower, bean, coffee, beet (for example sugar beet and fodder beet), peanut, oilseed rape, poppy, olive, coconut, cocoa, sugar cane, tobacco, vegetables (such as tomato, cucumbers, onions and lettuce), turf and ornamentals (see also below). The treatment of the seed of cereals (such as wheat, barley, rye, triticale and oats), maize and rice is of particular significance.

As also described below, the treatment of transgenic seed with the inventive active ingredients or compositions is of particular significance. This relates to the seed of plants containing at least one heterologous gene. Definition and examples of suitable heterologous genes are given below.

In the context of the present invention, the inventive composition is applied to the seed alone or in a suitable formulation. Preferably, the seed is treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again.

When treating the seed, care must generally be taken that the amount of the inventive composition applied to the seed and/or the amount of further additives is selected such that the germination of the seed is not impaired, or that the resulting plant is not damaged. This has to be borne in mind in particular in the case of active ingredients which can have phytotoxic effects at certain application rates.

The inventive compositions can be applied directly, i.e. without containing any other components and without having been diluted. In general, it is preferable to apply the compositions to the seed in the form of a suitable formulation. Suitable formulations and methods for seed treatment are known to those skilled in the art and are described, for example, in the following documents: U.S. Pat. No. 4,272,417, U.S. Pat. No. 4,245,432, U.S. Pat. No. 4,808,430, U.S. Pat. No. 5,876,739, US 2003/0176428 A1, WO 2002/080675, WO 2002/028186.

The active ingredients usable in accordance with the invention can be converted to the customary seed dressing formulations, such as solutions, emulsions, suspensions, powders, foams, slurries or other coating compositions for seed, and also ULV formulations.

These formulations are prepared in a known manner, by mixing the active ingredients with customary additives, for example customary extenders and also solvents or diluents, dyes, wetting agents, dispersants, emulsifiers, antifoams, preservatives, secondary thickeners, adhesives, gibberellins and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients. Preference is given to using alkyl naphthalenesulphonates, such as diisopropyl or diisobutyl naphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Usable with preference are non-ionic or anionic dispersants or mixtures of non-ionic or anionic dispersants. Suitable nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and aryl-sulphonate/formaldehyde condensates.

Antifoams which may be present in the seed dressing formulations usable in accordance with the invention are all foam-inhibiting substances conventionally used for the formulation of active agrochemical ingredients. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

The gibberellins which may be present in the seed dressing formulations usable in accordance with the invention may preferably be gibberellins A1, A3 (=gibberellic acid), A4 and A7; particular preference is given to using gibberellic acid. The gibberellins are known (cf. R. Wegler "Chemie der Pflanzenschutz-und Schädlings-bekämpfungsmittel" [Chemistry of the Crop Protection Compositions and Pesticides], vol. 2, Springer Verlag, 1970, p. 401-412).

The seed dressing formulations usable in accordance with the invention can be used, either directly or after previously having been diluted with water, for the treatment of a wide range of different seed, including the seed of transgenic plants. In this case, additional synergistic effects may also occur in interaction with the substances formed by expression.

For treatment of seed with the seed dressing formulations usable in accordance with the invention, or the preparations prepared therefrom by adding water, all mixing units usable customarily for the seed dressing are useful.

Specifically, the procedure in the seed dressing is to place the seed into a mixer, to add the particular desired amount of seed dressing formulations, either as such or after prior dilution with water, and to mix everything until the formulation is distributed homogeneously on the seed. If appropriate, this is followed by a drying process.

Mycotoxins

In addition, the inventive treatment can reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *F. acuminatum, F. asiaticum, F. avenaceum, F. crookwellense, F. culmorum, F. graminearum* (*Gibberella zeae*), *F. equiseti, F. fijikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides* etc., and also by *Aspergillus* spec., such as *A. flavus, A. parasiticus, A. nomius, A. ochraceus, A. clavatus, A. terreus, A. versicolor, Penicillium* spec., such as *P. verrucosum, P. viridicatum, P. citrinum, P. expansum, P. claviforme, P. roqueforti, Claviceps* spec., such as *C. purpurea, C. fisiformis, C. paspali, C. africana, Stachybotrys* spec. and others.

Material Protection

The inventive active ingredients or compositions can also be used in the protection of materials, for protection of industrial materials against attack and destruction by unwanted microorganisms, for example fungi and insects.

In addition, the inventive compounds can be used as antifouling compositions, alone or in combinations with other active ingredients.

Industrial materials in the present context are understood to mean inanimate materials which have been prepared for use in industry. For example, industrial materials which are to be protected by inventive active ingredients from microbial alteration or destruction may be adhesives, glues, paper, wallpaper and board/cardboard, textiles, carpets, leather, wood, fibers and tissues, paints and plastic articles, cooling lubricants and other materials which can be infected with or destroyed by microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials within the scope of the present invention preferably include adhesives, sizes, paper and card, leather, wood, paints, cooling lubricants and heat transfer fluids, more preferably wood.

The inventive active ingredients or compositions may prevent adverse effects, such as rotting, decay, discoloration, decoloration or formation of mould.

In the case of treatment of wood the compounds/compositions according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention or a composition according to the invention; this includes for example direct application, spraying, dipping, injection or any other suitable means.

In addition, the inventive compounds can be used to protect objects which come into contact with saltwater or brackish water, especially hulls, screens, nets, buildings, moorings and signalling systems, from fouling.

The inventive method for controlling unwanted fungi can also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The inventive active ingredients may prevent adverse effects, such as rotting, decay, discoloration, decoloration or formation of mould.

Microorganisms capable of degrading or altering the industrial materials include, for example, bacteria, fungi, yeasts, algae and slime organisms. The inventive active ingredients preferably act against fungi, especially moulds, wood-discoloring and wood-destroying fungi (Ascomycetes, Basidiomycetes, Deuteromycetes and Zygomycetes), and against slime organisms and algae. Examples include microorganisms of the following genera: *Alternaria*, such as *Alternaria tenuis; Aspergillus*, such as *Aspergillus niger; Chaetomium*, such as *Chaetomium globosum; Coniophora*, such as *Coniophora puetana; Lentinus*, such as *Lentinus tigrinus; Penicillium*, such as *Penicillium glaucum; Polyporus*, such as *Polyporus versicolor; Aureobasidium*, such as *Aureobasidium pullulans; Sclerophoma*, such as *Sclerophoma pityophila; Trichoderma*, such as *Trichoderma viride; Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp. and *Tyromyces* spp., *Cladosporium* spp., *Paecilomyces* spp. *Mucor* spp., *Escherichia*, such as *Escherichia coli; Pseudomonas*, such as *Pseudomonas aeruginosa; Staphylococcus*, such as *Staphylococcus aureus, Candida* spp. and *Saccharomyces* spp., such as *Saccharomyces cerevisae*.

Antimycotic Activity

In addition, the inventive active ingredients also have very good antimycotic activity. They have a very broad antimycotic activity spectrum, especially against dermatophytes and yeasts, moulds and diphasic fungi (for example against *Candida* species, such as *C. albicans, C. glabrata*), and *Epidermophyton floccosum, Aspergillus* species, such as *A. niger* and *A. fumigatus, Trichophyton* species, such as *T. mentagrophytes, Microsporon* species such as *M. canis* and *M. audouinii*. The list of these fungi by no means constitutes a restriction of the mycotic spectrum covered, and is merely of illustrative character.

The inventive active ingredients can therefore be used both in medical and in non-medical applications.

Application Rates and Timing

When using the inventive active ingredients as fungicides, the application rates can be varied within a relatively wide range, depending on the kind of application. The application rate of the inventive active ingredients is in the case of treatment of plant parts, for example leaves: from 0.1 to 10 000 g/ha, preferably from 10 to 1000 g/ha, more preferably from 10 to 800 g/ha, even more preferably from 50 to 300 g/ha (in the case of application by watering or dripping, it is even possible to reduce the application rate, especially when inert substrates such as rockwool or perlite are used);

in the case of seed treatment: from 2 to 200 g per 100 kg of seed, preferably from 3 to 150 g per 100 kg of seed, more preferably from 2.5 to 25 g per 100 kg of seed, even more preferably from 2.5 to 12.5 g per 100 kg of seed;

in the case of soil treatment: from 0.1 to 10 000 g/ha, preferably from 1 to 5000 g/ha.

These application rates are merely by way of example and are not limiting for the purposes of the invention.

The inventive active ingredients or compositions can thus be used to protect plants from attack by the pathogens mentioned for a certain period of time after treatment. The period for which protection is provided extends generally for 1 to 28 days, preferably for 1 to 14 days, more preferably for 1 to 10 days, most preferably for 1 to 7 days, after the treatment of the plants with the active ingredients, or for up to 200 days after a seed treatment.

The method of treatment according to the invention also provides the use or application of compounds (A) and (B) and/or (C) in a simultaneous, separate or sequential manner. If the single active ingredients are applied in a sequential manner, i.e. at different times, they are applied one after the other within a reasonably short period, such as a few hours or days. Preferably the order of applying the compounds (A) and (B) and/or (C) is not essential for working the present invention.

The plants listed can particularly advantageously be treated in accordance with the invention with the compounds of the general formula (I) and the inventive compositions. The preferred ranges stated above for the active ingredients or compositions also apply to the treatment of these plants. Particular emphasis is given to the treatment of plants with the compounds or compositions specifically mentioned in the present text.

The invention is illustrated by the examples below. However, the invention is not limited to the examples.

Preparation Examples

The compounds which follow can be prepared by one or more of the below mentioned processes.

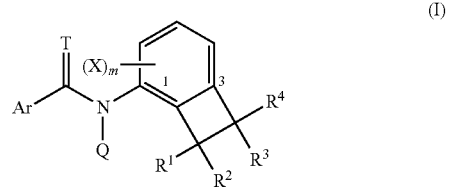

(I)

TABLE 1

| Ex No | Ar | $X^1$ | $X^2$ | $X^3$ | $X^4$ | T | Q | m | X | $R^1$ | $R^2$ | $R^3$ | $R^4$ | LogP |
|---|---|---|---|---|---|---|---|---|---|---|---|---|---|---|
| I-01 | Ar2 | difluoromethyl | H | — | — | C=O | H | 0 | H | H | H | phenyl | H | 3.20[a] |
| I-02 | Ar2 | difluoromethyl | fluoro | — | — | C=O | H | 0 | H | H | H | —(CH2)$_4$— | | 3.90[a] |
| I-03 | Ar2 | difluoromethyl | H | — | — | C=O | H | 0 | H | H | H | —(CH2)$_4$— | | 3.59[a] |
| I-04 | Ar2 | difluoromethyl | chloro | — | — | C=O | H | 0 | H | H | H | ethyl | ethyl | 4.36[a] |
| I-05 | Ar4 | difluoromethyl | H | H | H | C=O | H | 0 | H | H | H | methyl | ethyl | 3.31[a] |
| I-06 | Ar4 | difluoromethyl | H | H | H | C=O | H | 0 | H | H | H | propan-2-yl | H | 3.39[a] |
| I-07 | Ar2 | difluoromethyl | chloro | — | — | C=O | H | 0 | H | H | H | —(CH2)$_5$— | | 4.56[a] |
| I-08 | Ar2 | difluoromethyl | H | — | — | C=O | H | 0 | H | H | H | —(CH2)$_5$— | | 3.94[a] |
| I-09 | Ar4 | difluoromethyl | H | H | H | C=O | H | 0 | H | H | H | —(CH2)$_4$— | | 3.46[a] |
| I-10 | Ar2 | methyl | fluoro | — | — | C=O | H | 0 | H | H | H | —(CH2)$_5$— | | 3.87[a] |
| I-11 | Ar2 | difluoromethyl | chloro | — | — | C=O | H | 0 | H | H | H | phenyl | H | 3.71[a] |
| I-12 | Ar2 | difluoromethyl | chloro | — | — | C=O | H | 0 | H | H | H | methyl | ethyl | 3.96[a] |
| I-13 | Ar2 | difluoromethyl | H | — | — | C=O | H | 0 | H | H | H | methyl | ethyl | 3.44[a] |
| I-14 | Ar2 | difluoromethyl | fluoro | — | — | C=O | H | 0 | H | H | H | ethyl | ethyl | 4.11[a] |
| I-15 | Ar2 | difluoromethyl | fluoro | — | — | C=O | H | 0 | H | H | H | methyl | H | 3.02[a] |
| I-16 | Ar2 | difluoromethyl | chloro | — | — | C=O | H | 0 | H | H | H | propan-2-yl | H | 4.06[a] |
| I-17 | Ar4 | difluoromethyl | H | H | H | C=O | H | 0 | H | H | H | —(CH2)$_5$— | | 3.80[a] |
| I-18 | Ar2 | difluoromethyl | fluoro | — | — | C=O | H | 0 | H | H | H | —(CH2)$_5$— | | 4.31[a] |
| I-19 | Ar4 | difluoromethyl | H | H | H | C=O | H | 0 | H | H | H | phenyl | H | 3.06[a] |
| I-20 | Ar2 | difluoromethyl | H | — | — | C=O | H | 0 | H | H | H | propan-2-yl | H | 3.50[a] |
| I-21 | Ar2 | difluoromethyl | chloro | — | — | C=O | H | 0 | H | H | H | —(CH2)$_4$— | | 4.14[a] |

The compounds which follow can be prepared by one or more of the below mentioned processes.

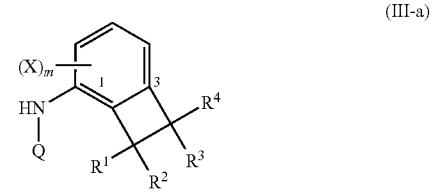

(III-a)

TABLE 2

| Ex No | Q | m | X | $R^1$ | $R^2$ | $R^3$ | $R^4$ | LogP |
|---|---|---|---|---|---|---|---|---|
| III-a-1 | H | 0 | H | H | H | —(CH$_2$)$_4$— | | 2.03[a] |
| III-a-2 | H | 0 | H | H | H | ethyl | ethyl | 2.32[a] |
| III-a-3 | H | 0 | H | H | H | H | methyl | 0.87[a] |
| III-a-4 | H | 0 | H | H | H | H | propan-2-yl | 1.90[a] |
| III-a-5 | H | 0 | H | H | H | methyl | methyl | 1.36[a] |

TABLE 2-continued

| Ex No | Q | m | X | $R^1$ | $R^2$ | $R^3$ | $R^4$ | | LogP |
|---|---|---|---|---|---|---|---|---|---|
| III-a-6 | H | 0 | H | H | H | methyl | ethyl | | 1.82[a] |
| III-a-7 | H | 0 | H | H | H | —(CH$_2$)$_5$— | | | 2.37[a] |
| III-a-8 | H | 0 | H | H | H | H | phenyl | | 2.20[a] |

Measurement of Log P values was performed according to EEC directive 79/831 Annex V.A8 by HPLC (High Performance Liquid Chromatography) on reversed phase columns with the following method:

[a] Log P value is determined by measurement of LC-UV, in an acidic range, with 0.1% formic acid in water and acetonitrile as eluent (linear gradient from 10% acetonitrile to 95% acetonitrile).

Calibration was done with straight-chain alkan2-ones (with 3 to 16 carbon atoms) with known Log P values (measurement of Log P values using retention times with linear interpolation between successive alkanones). Lambda-max-values were determined using UV-spectra from 200 nm to 400 nm and the peak values of the chromatographic signals.

NMR-Peak Lists

1H-NMR data of selected examples are written in form of 1H-NMR-peak lists. To each signal peak are listed the δ-value in ppm and the signal intensity in round brackets. Between the δ-value—signal intensity pairs are semicolons as delimiters.

The peak list of an example has therefore the form:

$\delta_1$ (intensity$_1$); $\delta_2$ (intensity$_2$); ... ; $\delta_i$ (intensity$_i$); ... ; $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1H-NMR peak lists are similar to classical 1H-NMR prints and contains therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-D$_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity>90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists you find in the publication "Citation of NMR Peaklist Data within Patent Applications" of the Research Disclosure Database Number 564025.

NMR Peak Lists Table 1

Example I-01: $^1$H-NMR (400.1 MHz, d$_6$-DMSO):
δ = 10.044 (3.5); 8.477 (3.9); 7.454 (1.5); 7.345 (1.6); 7.342 (0.8); 7.327 (4.4); 7.319 (4.1); 7.314 (1.7); 7.309 (4.5); 7.281 (5.9); 7.262 (7.4); 7.245 (3.8); 7.224 (2.9); 7.210 (0.6); 7.206 (0.9); 7.203 (0.5); 7.184 (1.7); 6.985 (1.8); 6.970 (1.6); 6.967 (1.5); 4.625 (1.2); 4.619 (1.4); 4.612 (1.4); 4.606 (1.2); 4.046 (0.4); 4.028 (0.5); 3.972 (16.0); 3.914 (0.4); 3.797 (1.3); 3.783 (1.4); 3.761 (1.6); 3.747 (1.4); 3.322 (13.7); 3.155 (1.5); 3.149 (1.5); 3.119 (1.4); 3.113 (1.4); 2.531 (0.6); 2.517 (10.8); 2.513 (21.9); 2.508 (29.6); 2.504 (21.0); 2.499 (9.8); 1.996 (1.6); 1.364 (0.5); 1.200 (0.5); 1.182 (0.9); 1.164 (0.5)

Example I-02: $^1$H-NMR (400.1 MHz, d$_6$-DMSO):
δ = 9.950 (0.3); 9.907 (4.5); 7.253 (0.6); 7.247 (2.4); 7.204 (2.3); 7.202 (2.6); 7.184 (5.3); 7.182 (4.9); 7.154 (2.9); 7.136 (3.4); 7.113 (6.5); 6.979 (2.7); 6.868 (3.9); 6.867 (4.1); 6.851 (3.6); 6.850 (3.5); 3.823 (16.0); 3.324 (41.3); 3.054 (11.7); 2.670 (0.3); 2.548 (0.6); 2.544 (0.6); 2.540 (0.5); 2.524 (0.8); 2.519 (1.3); 2.510 (19.9); 2.506 (41.7); 2.501 (56.9); 2.497 (40.0); 2.492 (18.3); 2.459 (0.5); 2.455 (0.6); 2.328 (0.4); 1.847 (3.0); 1.832 (6.4); 1.820 (5.2); 1.801 (1.6); 1.794 (2.2); 1.778 (2.3); 1.772 (2.4); 1.766 (2.7); 1.761 (2.9); 1.754 (3.2); 1.738 (3.1); 1.731 (2.4); 1.723 (1.9); 1.715 (1.4); 1.710 (1.3); 1.703 (0.9); 1.690 (0.6); 1.247 (1.0); 1.207 (1.9); 0.875 (0.5); 0.858 (1.7); 0.841 (0.6); 0.008 (0.5); 0.000 (15.7); −0.009 (0.5)

Example I-03: $^1$H-NMR (400.1 MHz, d$_6$-DMSO):
δ = 9.919 (3.5); 8.453 (3.9); 7.450 (1.6); 7.348 (0.3); 7.315 (4.0); 7.254 (0.3); 7.179 (1.9); 7.171 (1.0); 7.155 (7.0); 7.150 (4.6); 7.140 (3.0); 7.120 (0.7); 6.862 (2.2); 6.857 (1.9); 6.848 (2.2); 6.842 (2.0); 3.966 (16.0); 3.318 (12.3); 3.102 (9.7); 2.530 (0.4); 2.526 (0.7); 2.517 (9.7); 2.512 (20.5); 2.508 (28.6); 2.503 (21.1); 2.499 (10.8); 1.995 (0.9); 1.854 (2.2); 1.839 (4.8); 1.826 (4.2); 1.810 (1.5); 1.803 (1.9); 1.790 (1.8); 1.786 (1.8); 1.782 (2.1); 1.774 (2.2); 1.770 (2.4); 1.764 (2.7); 1.749 (2.6); 1.743 (2.1); 1.725 (1.2); 1.714 (0.8); 1.702 (0.6); 1.689 (0.4); 1.286 (0.6); 1.254 (2.6); 1.222 (1.8); 1.200 (0.4); 1.182 (0.6); 0.882 (1.2); 0.866 (4.1); 0.848 (1.6)

Example I-04: $^1$H-NMR (400.1 MHz, d$_6$-DMSO):
δ = 10.026 (2.9); 7.259 (1.8); 7.250 (1.7); 7.238 (2.4); 7.142 (1.6); 7.124 (2.4); 7.115 (3.4); 7.104 (1.4); 6.981 (1.6); 6.889 (2.9); 6.872 (2.6); 3.913 (14.2); 3.375 (0.4); 3.325 (33.1); 2.875 (4.6); 2.551 (0.4); 2.524 (0.4); 2.519 (0.7); 2.510 (10.5); 2.506 (22.2); 2.501 (30.4); 2.497 (21.4); 2.492 (9.8); 1.704 (0.4); 1.688 (1.2); 1.681 (1.1); 1.669 (3.5); 1.662 (3.3); 1.651 (3.6); 1.644 (3.7); 1.632 (1.3); 1.627 (1.4); 1.610 (0.5); 1.185 (0.4); 0.895 (7.1); 0.876 (16.0); 0.858 (6.5); 0.647 (0.4); 0.628 (0.5); 0.000 (8.6)

Example I-05: $^1$H-NMR (400.1 MHz, d$_6$-DMSO):
δ = 10.545 (3.2); 8.827 (2.3); 8.824 (2.5); 8.815 (2.5); 8.812 (2.5); 8.166 (1.9); 8.147 (2.1); 7.731 (1.5); 7.719 (1.6); 7.711 (1.6); 7.699 (1.4); 7.311 (3.2); 7.289 (3.4); 7.177 (5.1); 7.157 (2.8); 7.136 (1.8); 7.124 (0.4); 7.108 (0.4); 7.042 (2.1); 6.907 (3.5); 6.890 (3.1); 3.317 (15.6); 3.067 (1.6); 3.032 (2.9); 2.946 (3.1); 2.911 (1.8); 2.530 (0.9); 2.525 (1.3); 2.517 (12.7);

NMR Peak Lists Table 1

2.512 (26.0); 2.508 (35.8); 2.503 (25.9); 2.499 (13.1); 1.995 (0.8); 1.692 (0.9); 1.678 (2.4); 1.674 (2.3); 1.659 (2.6); 1.655 (2.6); 1.640 (1.2); 1.621 (0.4); 1.381 (0.4); 1.338 (16.0); 1.306 (0.7); 1.287 (1.1); 1.276 (1.7); 1.266 (1.7); 1.251 (4.6); 1.200 (0.4); 1.182 (0.6); 0.962 (4.1); 0.944 (8.8); 0.925 (4.0); 0.894 (0.6); 0.883 (2.0); 0.866 (6.5); 0.848 (2.5); 0.796 (0.4)
Example I-06: $^1$H-NMR (400.1 MHz, $d_6$-DMSO):
δ = 10.553 (5.9); 8.830 (4.1); 8.826 (4.4); 8.818 (4.4); 8.814 (4.3); 8.167 (3.4); 8.147 (3.7); 7.734 (2.7); 7.722 (2.8); 7.714 (2.7); 7.702 (2.4); 7.313 (5.8); 7.290 (5.7); 7.189 (3.5); 7.179 (8.4); 7.170 (5.1); 7.150 (2.9); 7.043 (3.9); 6.958 (6.0); 6.940 (5.1); 3.318 (34.9); 3.288 (2.5); 3.275 (2.6); 3.103 (1.4); 3.098 (1.7); 3.091 (1.5); 3.083 (2.1); 3.076 (1.8); 3.069 (1.5); 3.063 (1.3); 2.906 (2.8); 2.901 (2.6); 2.870 (2.4); 2.864 (2.3); 2.677 (0.4); 2.530 (0.9); 2.525 (1.5); 2.517 (20.8); 2.512 (42.9); 2.508 (58.3); 2.503 (41.0); 2.499 (19.0); 2.335 (0.4); 2.080 (1.8); 1.773 (0.4); 1.757 (1.1); 1.740 (1.7); 1.735 (1.4); 1.723 (1.5); 1.718 (1.7); 1.701 (1.2); 1.685 (0.5); 1.065 (15.6); 1.048 (14.9); 0.992 (16.0); 0.976 (15.3)
Example I-07: $^1$H-NMR (400.1 MHz, $d_6$-DMSO):
δ = 10.029 (3.4); 7.274 (2.2); 7.252 (3.9); 7.152 (1.7); 7.134 (2.5); 7.117 (4.4); 6.990 (3.1); 6.983 (2.2); 6.973 (2.5); 5.760 (0.5); 3.920 (16.0); 3.321 (68.3); 2.908 (6.8); 2.531 (0.5); 2.526 (0.8); 2.517 (11.3); 2.513 (23.4); 2.508 (32.0); 2.504 (22.7); 2.499 (10.7); 1.714 (0.6); 1.694 (1.6); 1.650 (3.8); 1.622 (2.7); 1.556 (1.3); 1.534 (2.3); 1.509 (1.5)
Example I-08: $^1$H-NMR (400.1 MHz, $d_6$-DMSO):
δ = 9.909 (3.4); 8.456 (3.9); 7.457 (1.6); 7.321 (3.8); 7.198 (1.9); 7.186 (2.0); 7.179 (3.8); 7.177 (3.7); 7.149 (2.0); 7.131 (2.4); 7.111 (1.3); 6.971 (2.6); 6.954 (2.2); 5.760 (9.3); 3.966 (16.0); 3.321 (17.3); 2.940 (8.7); 2.531 (0.4); 2.517 (7.7); 2.513 (15.9); 2.508 (21.9); 2.504 (16.2); 2.499 (8.3); 1.711 (0.6); 1.691 (1.6); 1.649 (4.1); 1.621 (2.8); 1.585 (0.7); 1.556 (1.3); 1.532 (2.1); 1.505 (1.7); 1.253 (0.5); 0.866 (0.6)
Example I-09: $^1$H-NMR (400.1 MHz, $d_6$-DMSO):
δ = 10.554 (5.8); 8.827 (4.1); 8.824 (4.4); 8.816 (4.4); 8.812 (4.3); 8.161 (3.3); 8.141 (3.6); 7.732 (2.6); 7.720 (2.8); 7.713 (2.6); 7.701 (2.4); 7.308 (3.4); 7.280 (4.2); 7.260 (6.1); 7.184 (3.6); 7.173 (8.1); 7.166 (5.1); 7.145 (2.8); 7.038 (3.8); 6.902 (6.3); 6.885 (5.6); 3.317 (36.0); 3.131 (16.0); 2.677 (0.4); 2.557 (0.3); 2.530 (1.0); 2.517 (23.6); 2.512 (48.6); 2.508 (65.8); 2.503 (46.5); 2.499 (21.7); 2.335 (0.4); 2.080 (4.0); 1.869 (4.5); 1.854 (9.2); 1.843 (7.4); 1.831 (3.1); 1.818 (2.5); 1.812 (2.8); 1.795 (3.2); 1.790 (3.5); 1.783 (3.7); 1.778 (4.2); 1.773 (4.9); 1.757 (4.6); 1.734 (2.1); 1.721 (1.3)
Example I-10: $^1$H-NMR (400.1 MHz, $d_6$-DMSO):
δ = 12.506 (0.5); 9.517 (0.5); 7.230 (0.4); 7.210 (0.6); 7.107 (0.4); 6.948 (0.5); 6.931 (0.4); 3.677 (2.2); 3.675 (2.2); 3.640 (8.2); 3.637 (8.4); 3.319 (2.2); 2.893 (1.4); 2.531 (0.5); 2.526 (0.6); 2.517 (6.3); 2.513 (13.0); 2.508 (17.8); 2.504 (12.9); 2.499 (6.4); 2.469 (0.4); 2.464 (0.4); 2.459 (0.4); 2.269 (4.4); 2.261 (16.0); 1.995 (0.4); 1.644 (0.7); 1.615 (0.5); 1.530 (0.4); 1.243 (0.4)
Example I-11: $^1$H-NMR (400.1 MHz, $d_6$-DMSO):
δ = 10.177 (3.6); 7.348 (3.5); 7.329 (7.4); 7.316 (1.5); 7.311 (4.6); 7.282 (5.9); 7.269 (3.3); 7.265 (3.3); 7.260 (3.5); 7.249 (3.1); 7.245 (2.0); 7.241 (1.1); 7.230 (2.4); 7.227 (2.7); 7.222 (0.7); 7.213 (0.6); 7.209 (0.9); 7.206 (0.5); 7.126 (4.2); 7.008 (3.0); 6.991 (4.1); 4.643 (1.2); 4.637 (1.5); 4.630 (1.5); 4.624 (1.3); 3.923 (16.0); 3.904 (0.3); 3.873 (0.3); 3.843 (0.5); 3.771 (1.1); 3.757 (1.2); 3.735 (1.4); 3.721 (1.2); 3.625 (0.6); 3.623 (0.5); 3.619 (0.4); 3.615 (0.6); 3.609 (1.6); 3.603 (0.6); 3.598 (0.4); 3.594 (0.5); 3.592 (0.7); 3.324 (1.5); 3.113 (1.1); 3.107 (1.1); 3.076 (1.0); 3.071 (1.0); 2.517 (5.7); 2.513 (12.0); 2.508 (16.5); 2.504 (11.9); 2.499 (5.7); 1.782 (0.6); 1.774 (0.7); 1.766 (1.9); 1.761 (0.5); 1.757 (0.7); 1.749 (0.7); 1.366 (0.6); 1.096 (0.4); 1.078 (0.7); 1.061 (0.4)
Example I-12: $^1$H-NMR (400.1 MHz, $d_6$-DMSO):
δ = 10.030 (2.9); 7.267 (2.0); 7.247 (3.1); 7.153 (1.6); 7.135 (2.3); 7.116 (4.5); 6.982 (1.7); 6.882 (3.0); 6.865 (2.6); 3.920 (15.0); 3.317 (7.6); 3.010 (1.0); 2.975 (1.9); 2.889 (2.1); 2.853 (1.2); 2.530 (0.3); 2.517 (7.0); 2.512 (14.1); 2.508 (18.9); 2.503 (13.3); 2.499 (6.2); 1.684 (0.7); 1.681 (0.8); 1.666 (2.2); 1.662 (2.1); 1.647 (2.3); 1.643 (2.2); 1.627 (0.9); 1.370 (0.4); 1.327 (16.0); 1.254 (0.3); 1.241 (0.6); 0.953 (3.9); 0.934 (8.6); 0.916 (3.5); 0.884 (0.5); 0.866 (0.6)
Example I-13: $^1$H-NMR (400.1 MHz, $d_6$-DMSO):
δ = 9.906 (3.1); 8.453 (3.8); 7.452 (1.5); 7.317 (3.5); 7.193 (1.7); 7.182 (1.9); 7.174 (3.8); 7.150 (2.0); 7.132 (2.3); 7.112 (1.1); 6.864 (2.6); 6.848 (2.4); 3.965 (15.8); 3.317 (12.0); 3.043 (1.6); 3.008 (2.9); 2.919 (3.1); 2.884 (1.8); 2.530 (0.6); 2.516 (13.7); 2.512 (27.4); 2.508 (36.4); 2.503 (26.0); 2.499 (12.5); 1.682 (0.7); 1.678 (0.8); 1.664 (2.2); 1.659 (2.1); 1.645 (2.3); 1.641 (2.2); 1.625 (0.9); 1.367 (0.4); 1.324 (16.0); 1.251 (1.1); 0.950 (4.0); 0.931 (8.7); 0.913 (3.6); 0.882 (0.6); 0.865 (0.9); 0.848 (0.3)
Example I-14: $^1$H-NMR (400.1 MHz, $d_6$-DMSO):
δ = 9.885 (2.8); 7.258 (1.5); 7.225 (1.9); 7.205 (3.0); 7.141 (1.6); 7.136 (0.4); 7.124 (5.4); 7.103 (1.2); 6.990 (1.7); 6.883 (2.7); 6.867 (2.4); 3.824 (10.0); 3.327 (11.9); 2.869 (6.3); 2.519 (0.4); 2.511 (4.8); 2.506 (10.1); 2.502 (13.8); 2.497 (9.7); 2.493 (4.4); 1.722 (0.4); 1.703 (0.4); 1.687 (1.1); 1.684 (1.1); 1.679 (1.1); 1.669 (3.4); 1.661 (3.2); 1.650 (3.4); 1.643 (3.5); 1.631 (1.2); 1.625 (1.3); 1.608 (0.7); 1.246 (0.4); 1.187 (0.5); 0.892 (7.0); 0.873 (16.0); 0.855 (6.5); 0.841 (0.5); 0.644 (0.4); 0.625 (0.7); 0.000 (3.5)
Example I-15: $^1$H-NMR (400.1 MHz, $d_6$-DMSO):
δ = 9.916 (4.1); 7.251 (2.6); 7.229 (2.8); 7.208 (4.9); 7.163 (2.7); 7.145 (3.2); 7.124 (2.0); 7.117 (5.8); 6.983 (2.8); 6.879 (4.0); 6.862 (3.6); 3.824 (16.0); 3.441 (0.8); 3.436 (0.8); 3.423 (1.4); 3.411 (1.0); 3.406 (1.1); 3.385 (2.2); 3.372 (1.2); 3.350 (2.2); 3.337 (1.7); 3.325 (27.6); 2.724 (2.0); 2.719 (1.9); 2.688 (1.8); 2.684 (1.7); 2.546 (0.4); 2.543 (0.4); 2.524 (0.5); 2.519 (0.8); 2.510 (11.8); 2.506 (24.8); 2.501 (33.9); 2.497 (24.0); 2.492 (11.0); 2.459 (0.4); 1.360 (0.8); 1.330 (12.5); 1.312 (12.0); 1.209 (0.7); 1.192 (0.7); 0.000 (8.6)
Example I-16: $^1$H-NMR (400.1 MHz, $d_6$-DMSO):
δ = 10.107 (0.4); 10.037 (3.0); 7.279 (2.0); 7.258 (3.1); 7.253 (2.5); 7.168 (1.6); 7.149 (2.2); 7.129 (1.5); 7.125 (1.0); 7.118 (3.9); 6.990 (0.4); 6.984 (1.9); 6.932 (3.0); 6.914 (2.5); 3.922 (16.0); 3.317 (12.3); 3.267 (0.9); 3.254 (1.1); 3.231 (1.1); 3.218 (1.2); 3.089 (0.7); 3.083 (0.8); 3.076 (0.7); 3.068 (1.0); 3.061 (0.9); 3.054 (0.8); 3.048 (0.7); 2.851 (1.1); 2.846 (1.1); 2.815 (1.0); 2.810 (1.0); 2.530 (0.5); 2.526 (0.9); 2.517 (10.8); 2.512 (22.5); 2.508 (31.2); 2.503 (23.0); 2.499 (11.8); 1.744 (0.7); 1.728 (1.0); 1.722 (0.8); 1.711 (0.8); 1.705 (0.9); 1.695 (0.5); 1.689 (0.7); 1.191 (1.1); 1.173 (1.1); 1.056 (8.1); 1.040 (7.9); 0.984 (8.5); 0.967 (8.4); 0.922 (1.2); 0.905 (1.2); 0.866 (0.4); 0.745 (1.1); 0.729 (1.0)
Example I-17: $^1$H-NMR (400.1 MHz, $d_6$-DMSO):
δ = 10.547 (6.3); 8.828 (4.1); 8.825 (4.5); 8.816 (4.6); 8.813 (4.5); 8.167 (3.5); 8.148 (3.9); 7.732 (2.7); 7.720 (3.0); 7.712 (2.9); 7.700 (2.7); 7.312 (5.6); 7.290 (6.2); 7.179 (7.7); 7.174 (4.1); 7.155 (5.1); 7.135 (3.2); 7.044 (3.6); 7.016 (6.2); 6.999 (5.1); 5.761 (2.0); 3.318 (46.9); 2.964 (16.0); 2.677 (0.5); 2.673 (0.3); 2.531 (1.3); 2.517 (26.2); 2.513 (53.8); 2.508 (73.7); 2.504 (54.6); 2.500 (28.2); 2.340 (0.4); 2.335 (0.5); 2.331 (0.4); 1.726 (1.4); 1.704 (3.5); 1.662 (8.5); 1.634 (6.1); 1.565 (2.8); 1.544 (5.0); 1.521 (3.5); 1.253 (0.4); 1.156 (0.7); 0.867 (0.4)
Example I-18: $^1$H-NMR (400.1 MHz, $d_6$-DMSO):
δ = 9.887 (4.4); 7.258 (2.3); 7.236 (3.1); 7.216 (4.7); 7.150 (2.3); 7.132 (3.5); 7.124 (5.7); 7.112 (2.0); 6.990 (3.7); 6.986 (4.3); 6.968 (3.2); 5.761 (10.0); 3.830 (16.0); 3.318 (31.7); 2.898 (10.9); 2.530 (0.8); 2.517 (17.5); 2.513 (35.5); 2.508

NMR Peak Lists Table 1

(47.9); 2.504 (33.7); 2.499 (15.7); 1.711 (0.8); 1.691 (2.2); 1.647 (5.1); 1.633 (2.9); 1.620 (3.5); 1.555 (1.6); 1.532 (2.9); 1.508 (2.1); 1.145 (0.5); 0.866 (0.4)
Example I-19: $^1$H-NMR (400.1 MHz, $d_6$-DMSO):
δ = 10.674 (7.6); 8.823 (5.1); 8.820 (5.2); 8.811 (5.2); 8.808 (4.9); 8.171 (4.2); 8.151 (4.4); 7.729 (3.4); 7.717 (3.5); 7.709 (3.2); 7.697 (2.9); 7.367 (4.9); 7.347 (9.2); 7.330 (10.8); 7.312 (11.3); 7.304 (5.0); 7.285 (16.0); 7.267 (11.7); 7.247 (5.9); 7.244 (4.6); 7.226 (5.5); 7.212 (1.2); 7.208 (1.9); 7.169 (9.3); 7.034 (5.0); 7.024 (6.7); 7.006 (5.7); 4.644 (3.5); 4.636 (3.5); 4.037 (0.3); 4.020 (0.3); 3.817 (2.6); 3.803 (2.8); 3.781 (3.2); 3.767 (2.9); 3.669 (0.8); 3.655 (0.4); 3.642 (0.4); 3.630 (0.4); 3.625 (0.4); 3.618 (0.8); 3.609 (0.5); 3.601 (0.9); 3.598 (0.7); 3.589 (1.4); 3.570 (5.9); 3.552 (0.7); 3.546 (1.0); 3.543 (1.0); 3.536 (1.2); 3.530 (0.6); 3.519 (5.8); 3.514 (6.3); 3.470 (4597.6); 3.420 (31.0); 3.415 (9.0); 3.390 (2.6); 3.372 (5.3); 3.345 (1.3); 3.340 (0.4); 3.333 (0.7); 3.327 (0.6); 3.311 (0.4); 3.301 (0.4); 3.160 (3.3); 3.154 (3.4); 3.124 (3.1); 3.118 (3.0); 2.682 (0.5); 2.678 (0.6); 2.673 (0.5); 2.531 (1.3); 2.518 (34.8); 2.513 (72.9); 2.509 (99.6); 2.504 (71.2); 2.500 (33.5); 2.463 (0.8); 2.459 (0.9); 2.454 (0.7); 2.340 (0.5); 2.335 (0.7); 2.331 (0.5); 1.986 (1.4); 1.241 (0.3); 1.191 (0.4); 1.173 (0.8); 1.156 (0.4); 0.855 (0.5)
Example I-20: $^1$H-NMR (400.1 MHz, $d_6$-DMSO):
δ = 9.916 (3.5); 8.492 (0.5); 8.460 (3.8); 7.507 (0.6); 7.458 (1.5); 7.345 (0.5); 7.323 (3.7); 7.242 (0.4); 7.210 (0.4); 7.203 (1.4); 7.188 (2.2); 7.183 (3.6); 7.164 (2.1); 7.146 (2.2); 7.126 (1.0); 6.915 (2.6); 6.898 (2.3); 3.967 (16.0); 3.318 (9.9); 3.295 (1.0); 3.281 (1.3); 3.258 (1.3); 3.245 (1.4); 3.077 (0.6); 3.071 (0.8); 3.064 (0.7); 3.056 (1.0); 3.049 (0.8); 3.042 (0.7); 3.036 (0.6); 2.887 (1.4); 2.881 (1.3); 2.851 (1.2); 2.845 (1.2); 2.530 (0.4); 2.517 (9.8); 2.512 (19.9); 2.508 (26.9); 2.503 (19.0); 2.499 (8.9); 1.743 (0.6); 1.737 (0.5); 1.726 (0.9); 1.720 (0.8); 1.709 (0.8); 1.704 (0.9); 1.687 (0.6); 1.286 (0.3); 1.254 (1.6); 1.198 (1.2); 1.181 (1.2); 1.055 (8.2); 1.038 (7.8); 0.984 (8.6); 0.968 (8.2); 0.925 (1.2); 0.908 (1.2); 0.882 (0.8); 0.865 (2.5); 0.848 (1.0); 0.747 (1.2); 0.730 (1.2)
Example I-21: $^1$H-NMR (400.1 MHz, $d_6$-DMSO):
δ = 10.038 (3.2); 7.264 (0.4); 7.248 (2.7); 7.229 (3.3); 7.162 (1.8); 7.144 (2.4); 7.124 (1.6); 7.112 (4.1); 6.978 (2.0); 6.877 (3.2); 6.860 (2.8); 3.919 (16.0); 3.316 (14.2); 3.073 (7.7); 2.530 (0.7); 2.517 (13.7); 2.512 (27.6); 2.508 (37.0); 2.503 (25.9); 2.499 (11.9); 1.858 (2.3); 1.843 (4.8); 1.831 (3.8); 1.803 (1.6); 1.790 (1.6); 1.787 (1.7); 1.782 (1.9); 1.773 (2.1); 1.769 (2.2); 1.764 (2.6); 1.748 (2.5); 1.741 (1.9); 1.725 (1.1); 1.720 (1.1); 1.712 (0.7); 1.700 (0.5); 1.287 (0.5); 1.255 (2.5); 1.216 (1.7); 0.883 (1.2); 0.866 (3.8); 0.848 (1.4)

NMR Peak Lists Table 2

Example III-a-5: $^1$H-NMR (400.1 MHz, $d_6$-DMSO):
δ = 6.846 (0.5); 6.827 (0.8); 6.808 (0.6); 6.342 (1.2); 6.340 (1.2); 6.321 (1.1); 6.320 (1.1); 6.264 (1.1); 6.246 (1.0); 4.877 (1.2); 3.328 (56.0); 2.706 (3.8); 2.517 (2.7); 2.513 (5.6); 2.508 (7.6); 2.504 (5.3); 2.499 (2.5); 1.319 (16.0)
Example III-a-7: $^1$H-NMR (299.9 MHz, $d_6$-DMSO):
δ = 6.836 (1.8); 6.811 (3.3); 6.786 (2.3); 6.380 (4.2); 6.356 (8.2); 6.329 (4.1); 4.876 (7.1); 3.320 (26.1); 2.611 (16.0); 2.506 (6.1); 2.500 (8.2); 2.494 (6.1); 1.884 (0.4); 1.857 (0.3); 1.640 (2.2); 1.602 (9.9); 1.561 (4.3); 1.520 (2.9); 1.505 (3.4); 1.418 (1.4); 1.334 (0.5); 1.270 (0.4); 1.261 (0.5); 1.232 (0.4); 1.078 (0.6); −0.001 (1.4)
Example III-a-8: $^1$H-NMR (299.9 MHz, $d_6$-DMSO):
δ = 7.322 (3.3); 7.297 (9.8); 7.273 (11.2); 7.243 (16.0); 7.219 (9.6); 7.190 (5.2); 7.167 (1.9); 6.952 (3.6); 6.926 (6.6); 6.901 (4.4); 6.437 (7.9); 6.410 (7.1); 6.369 (7.2); 6.345 (6.6); 5.031 (14.8); 4.517 (4.2); 4.506 (4.2); 3.514 (3.9); 3.496 (4.0); 3.470 (4.6); 3.452 (4.3); 3.315 (46.0); 2.805 (4.8); 2.797 (4.9); 2.760 (4.2); 2.753 (4.3); 2.505 (20.5); 2.500 (27.8); 2.494 (22.1); 1.250 (0.7); −0.001 (11.8)

Experimental Examples

General Procedure for Process a 3 ml of tetrahydrofuran and aminobenzocyclobutane of formula (III-a) (1 eq.) were charged into a Radley tube; Triethylamine (0.17 ml, 1.2 eq) was added dropwise and the reaction mixture was stirred at room temperature during 10 minutes. Acid chloride (1.1 eq.) diluted in 1 ml of tetrahydrofuran was then added dropwise and the mixture was refluxed for 2 hours. The reaction mixture was cooled at room temperature, and 4 ml of water was added. The aqueous phase was extracted with dichloromethane, washed with water and dried on a Chem Elut. The expected product was obtained with a good purity, sometimes without any purification, or by purification on silica gel column chromatography (yield: 65% to 95%).

General Procedure for Process a 3 ml of tetrahydrofuran and the carboxylic acid of formula (II) (1.1 eq.) were charged into a Radley tube. Triethylamine (2 eq.) was added dropwise, then 4 eq. of Polyphosphonic anhydride was added. The reaction mixture was stirred at room temperature during 30 minutes. 1 eq. of the aminobenzocyclobutane of formula (III-a) diluted on 1 ml of tetrahydrofuran was added dropwise. The mixture was refluxed overnight. The crude mixture was cooled at room temperature, and 4 ml of water was added. The aqueous phase was extracted with dichloromethane, washed with water and dried on a Chem Elut. The expected product was obtained with a good purity, sometimes without any purification, or by purification on silica gel column chromatography or HPLC prep. (yield=35% to 74%)

General Procedure for Process c

In a sealed microwave tube filled with Argon, 500 mg of the 1-bromobenzocyclobutane of formula (III-b) (1 eq) was dissolved in 20 ml of 1,4-Dioxane. 324 mg of terbutylcarbamate (1.5 eq), 117 mg of xantphos (0.1 eq), 1.2 g of Cesium carbonate (2 eq) and 41 mg of Palladium (II) acetate (0.1 eq) were consecutively added. The tube was sealed and warmed to 100° C. during 24 h. The crude mixture was cooled at room temperature, and water was added. The aqueous phase was extracted with dichloromethane, washed with water and dried on a Chem Elut. The expected product of formula (III-a) was obtained in 51% yield after silica gel column chromatography General Procedure for Process d To a stirred solution of compound of formula (w) (0.3 g) in pentane/diethyl ether (4:1) is added t-BuLi (3.2 eq.) at −78° C. The reaction was stirred for 5 mn and anhydrous THF (1 ml) was added, stirred for another 10 min. The mixture was allowed to warm to room temperature. After 30 mn, anhydrous 1,2-dibromoethane (0.5 ml) was added and stirred for 30 min. The reaction mixture was quenched with ice water at 0° C. and extracted with ethyl acetate. The organic layer was washed with water, brine and evaporated to obtain 0.15 g bromo compound of formula (III-b) which was purified by column chromatography General Procedure for Process f To a solution of carboxylic acid (III-d) (1.0 eq.) in acetone (40 ml) at 0° C., TEA (1.5 eq.), iso-Butyl chloroformate (1.3 eq.) were added drop wise and the reaction mixture was stirred for 30 minutes, then NaN3 (2.0 eq.) in water (5.0 ml) was added to the reaction mixture and stirred for 30 minutes. After completion of reaction, the reaction mixture was diluted with ice water and extracted with ethyl acetate. The combined organic layers were washed with brine solution, dried over anhydrous sodium sulfate and the solvent was removed under reduced pressure to get crude acyl azide.

The stirred solution of the above acyl azide (1.0 eq.) in benzyl alcohol (4.0 ml) was heated to 80° C. for 16 hours. The crude reaction mixture was purified by column chromatography by eluting with 15% EtOAc/Pet ether to afford the protected amine (81%).

To a solution of the above protected amine (1.0 eq.) in MeOH (20 ml) at room temperature, was added 10% Pd/C (180 mg) and the reaction mixture was stirred under hydrogen for 4 hours. After completion of reaction, the reaction mixture was filtered through Celite bed and filtrate was concentrated under reduced pressure to get crude product. This crude product was purified over silica gel column chromatography by eluting with 20% EtOAc/Pet ether to afford free amine (III-c)

Process g

To a stirred solution of aldehyde (III-e) (1.0 eq.) in Acetone:water (1:1, 40 ml) at 0° C., sulphamic acid (1.1 eq.), NaClO$_2$ (2.0 g, 23 mmol, 1.1 eq.) were added and the reaction mixture was stirred at room temperature for one hour. After completion of reaction, the reaction mixture was diluted with ice water and extracted with ethyl acetate. The combined organic layers were washed with brine solution, dried over anhydrous sodium sulfate and the solvent was removed under reduced pressure to get 83% of the desired carboxylic acid (III-d)

Process h

To a solution of the aryl compound (vv) (1.0 eq.) in pentane:diethyl ether (5:1, 36 ml) at −78° C., 1.6M t-BuLi in pentane (3.2 eq.) was added and the reaction mixture was stirred for 5 minutes, then anhydrous THF (5.0 ml) was added stirring was continued for 10 minutes. The reaction mixture was warmed to room temperature over a period of 30 minutes, then anhydrous DMF (1.0 eq.) was added and stirring was continued for 30 minutes. After completion of reaction, the reaction mixture was quenched with ice water at 0° C. and extracted with diethyl ether. The combined organic layer was washed with brine solution, dried over anhydrous sodium sulfate and the solvent was removed under reduced pressure to get crude product. This crude product was purified over silica gel column chromatography by eluting with 7-10% EtOAc/Pet ether to afford the expected aldehyde (III-e) (29%)

Example: In Vivo Preventive Test on *Botrytis cinerea* (Grey Mould)

| | |
|---|---|
| Solvent: | 5% by volume of Dimethyl sulfoxide |
| | 10% by volume of Acetone |
| Emulsifier: | 1 μl of Tween® 80 per mg of active ingredient |

The active ingredients are made soluble and homogenized in a mixture of Dimethyl sulfoxide/Acetone/Tween® 80 and then diluted in water to the desired concentration.

The young plants of gherkin are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Botrytis cinerea* spores. The contaminated gherkin plants are incubated for 4 to 5 days at 17° C. and at 90% relative humidity.

The test is evaluated 4 to 5 days after the inoculation. 0% means an efficacy which corresponds to that of the control plants while an efficacy of 100% means that no disease is observed.

In this test the following compounds according to the invention showed efficacy between 70% and 79% at a concentration of 500 ppm of active ingredient: I-04

In this test the following compounds according to the invention showed efficacy between 90% and 100% at a concentration of 500 ppm of active ingredient: I-02; I-14; I-15

In this test the following compounds according to the invention showed efficacy between 90% and 100% at a concentration of 100 ppm of active ingredient: I-06; I-19

Example: In Vivo Preventive Test on *Puccinia recondita* (Brown Rust on Wheat)

| | |
|---|---|
| Solvent: | 5% by volume of Dimethyl sulfoxide |
| | 10% by volume of Acetone |
| Emulsifier: | 1 μl of Tween® 80 per mg of active ingredient |

The active ingredients are made soluble and homogenized in a mixture of Dimethyl sulfoxide/Acetone/Tween® 80 and then diluted in water to the desired concentration.

The young plants of wheat are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Puccinia recondita* spores. The contaminated wheat plants are incubated for 24 hours at 20° C. and at 100% relative humidity and then for 10 days at 20° C. and at 70-80% relative humidity.

The test is evaluated 11 days after the inoculation. 0% means an efficacy which corresponds to that of the control plants while an efficacy of 100% means that no disease is observed.

In this test the following compounds according to the invention showed efficacy between 90% and 100% at a concentration of 500 ppm of active ingredient: I-02; I-04; I-14; I-15

In this test the following compounds according to the invention showed efficacy between 90% and 100% at a concentration of 100 ppm of active ingredient: I-01; I-03; I-05; I-06; I-07; I-08; I-09; I-11; I-12; I-13; I-16; I-17; I-18; I-19; I-20; I-21

Example: In Vivo Preventive Test on *Septoria tritici* (Leaf Spot on Wheat)

| | |
|---|---|
| Solvent: | 5% by volume of Dimethyl sulfoxide |
| | 10% by volume of Acetone |
| Emulsifier: | 1 µl of Tween ® 80 per mg of active ingredient |

The active ingredients are made soluble and homogenized in a mixture of Dimethyl sulfoxide/Acetone/Tween® 80 and then diluted in water to the desired concentration.

The young plants of wheat are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Septoria tritici* spores. The contaminated wheat plants are incubated for 72 hours at 18° C. and at 100% relative humidity and then for 21 days at 20° C. and at 90% relative humidity.

The test is evaluated 24 days after the inoculation. 0% means an efficacy which corresponds to that of the control plants while an efficacy of 100% means that no disease is observed.

In this test the following compounds according to the invention showed efficacy between 80% and 89% at a concentration of 500 ppm of active ingredient: I-02; I-04

In this test the following compounds according to the invention showed efficacy between 90% and 100% at a concentration of 500 ppm of active ingredient: I-14; I-15

In this test the following compounds according to the invention showed efficacy between 70% and 79% at a concentration of 100 ppm of active ingredient: I-05; I-06

In this test the following compounds according to the invention showed efficacy between 80% and 89% at a concentration of 100 ppm of active ingredient: I-01; I-07; I-11; I-18; I-19; I-20

Example: In Vivo Preventive Test on *Sphaerotheca fuliginea* (Powdery Mildew on Cucurbits)

| | |
|---|---|
| Solvent: | 5% by volume of Dimethyl sulfoxide |
| | 10% by volume of Acetone |
| Emulsifier: | 1 µl of Tween ® 80 per mg of active ingredient |

The active ingredients are made soluble and homogenized in a mixture of Dimethyl sulfoxide/Acetone/Tween® 80 and then diluted in water to the desired concentration.

The young plants of gherkin are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Sphaerotheca fuliginea* spores. The contaminated gherkin plants are incubated for 72 hours at 18° C. and at 100% relative humidity and then for 12 days at 20° C. and at 70-80% relative humidity.

The test is evaluated 15 days after the inoculation. 0% means an efficacy which corresponds to that of the control plants while an efficacy of 100% means that no disease is observed.

In this test the following compounds according to the invention showed efficacy between 80% and 89% at a concentration of 500 ppm of active ingredient: I-04

In this test the following compounds according to the invention showed efficacy between 90% and 100% at a concentration of 500 ppm of active ingredient: I-02; I-14; I-15

In this test the following compounds according to the invention showed efficacy between 80% and 89% at a concentration of 100 ppm of active ingredient: I-05; I-19

In this test the following compounds according to the invention showed efficacy between 90% and 100% at a concentration of 100 ppm of active ingredient: I-06; I-17

In this test the following compounds according to the invention showed efficacy between 90% and 100% at a concentration of 10 ppm of active ingredient: I-11

Example: In Vivo Preventive Test on *Uromyces appendiculatus* (Bean Rust)

| | |
|---|---|
| Solvent: | 5% by volume of Dimethyl sulfoxide |
| | 10% by volume of Acetone |
| Emulsifier: | 1 µl of Tween ® 80 per mg of active ingredient |

The active ingredients are made soluble and homogenized in a mixture of Dimethyl sulfoxide/Acetone/Tween® 80 and then diluted in water to the desired concentration.

The young plants of bean are treated by spraying the active ingredient prepared as described above. Control plants are treated only with an aqueous solution of Acetone/Dimethyl sulfoxide/Tween® 80.

After 24 hours, the plants are contaminated by spraying the leaves with an aqueous suspension of *Uromyces appendiculatus* spores. The contaminated bean plants are incubated for 24 hours at 20° C. and at 100% relative humidity and then for 10 days at 20° C. and at 70-80% relative humidity.

The test is evaluated 11 days after the inoculation. 0% means an efficacy which corresponds to that of the control plants while an efficacy of 100% means that no disease is observed.

In this test the following compounds according to the invention showed efficacy between 90% and 100% at a concentration of 500 ppm of active ingredient: I-02; I-04; I-14; I-15

In this test the following compounds according to the invention showed efficacy between 90% and 100% at a concentration of 100 ppm of active ingredient: I-01; I-03; I-05; I-06; I-07; I-08; I-09; I-11; I-12; I-13; I-16; I-17; I-18; I-19; I-20; I-21

Example: In Vivo Preventive Test on *Phakopsora* Test (Soybeans)

| | |
|---|---|
| Solvent: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of the causal agent of soybean rust (*Phakopsora pachyrhizi*) and stay for 24 h without light in an incubation cabinet at approximately 24° C. and a relative atmospheric humidity of 95%.

The plants remain in the incubation cabinet at approximately 24° C. and a relative atmospheric humidity of approximately 80% and a day/night interval of 12 h.

The test is evaluated 7 days after the inoculation. 0% means an efficacy which corresponds to that of the untreated control, while an efficacy of 100% means that no disease is observed.

In this test the following compounds according to the invention showed efficacy between 70% and 79% at a concentration of 10 ppm of active ingredient: I-17

In this test the following compounds according to the invention showed efficacy between 80% and 89% at a concentration of 10 ppm of active ingredient: I-05; I-13

The invention claimed is:

1. Benzocyclobutane(thio) carboxamide of formula (I)

(I)

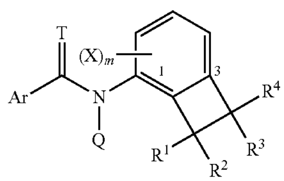

in which

Ar represents a radical selected from the group Ar1 to Ar15:

Ar1

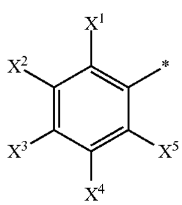

Ar2

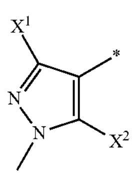

Ar3

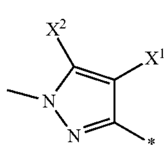

Ar4

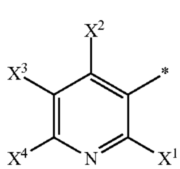

-continued

Ar5

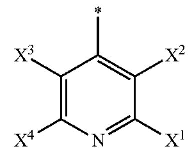

Ar6

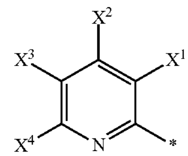

Ar7

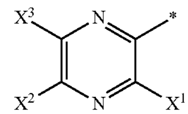

Ar8

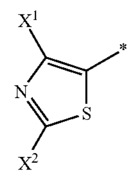

Ar9

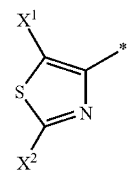

Ar10

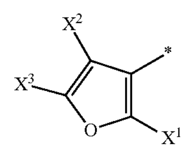

Ar11

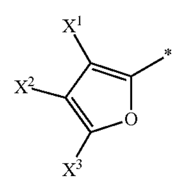

Ar12

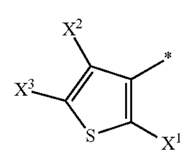

Ar13

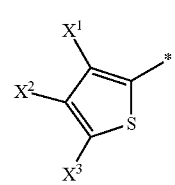

Ar14

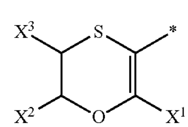

-continued

Ar15

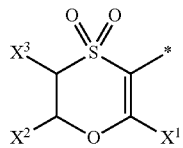

$X^1$, $X^2$, $X^3$, $X^4$ and $X^5$ independently represent hydrogen; halogen; cyano; nitro, hydroxyl; $C_1$-$C_{16}$-alkyl, $C_1$-$C_6$-haloalkyl having 1 to 9 identical or different halogen atoms; $C_3$-$C_7$-cycloalkyl, $C_3$-$C_7$-halocycloalkyl having 1 to 9 identical or different halogen atoms; $C_1$-$C_6$-alkoxy; or $C_1$-$C_6$-haloalkoxy having 1 to 9 identical or different halogen atoms;

T represents an oxygen or sulfur atom;

Q represents hydrogen, $C_1$-$C_6$-alkylsulfonyl, $C_1$-$C_4$-alkoxy-$C_1$-$C_4$-alkyl, $C_1$-$C_4$-haloalkylsulfonyl, or halo-$C_1$-$C_4$-alkoxy-$C_1$-$C_4$-alkyl;

X represents halogen, nitro, cyano, $C_1$-$C_{12}$-alkyl; $C_1$-$C_6$-haloalkyl having 1 to 9 identical or different halogen atoms; $C_1$-$C_6$-alkoxy; $C_1$-$C_6$-haloalkoxy having 1 to 9 identical or different halogen atoms; $C_1$-$C_6$-alkylsulfanyl; $C_1$-$C_6$-haloalkylsulfanyl having 1 to 9 identical or different halogen atoms; $C_1$-$C_6$-alkylsulfinyl; $C_1$-$C_6$-haloalkylsulfinyl having 1 to 9 identical or different halogen atoms; $C_1$-$C_6$-alkylsulfonyl; $C_1$-$C_6$-haloalkylsulfonyl having 1 to 9 identical or different halogen atoms; $C_2$-$C_{12}$-alkenyl; $C_2$-$C_{12}$-alkynyl; $C_3$-$C_7$-cycloalkyl; phenyl; or tri($C_1$-$C_8$)alkylsilyl; tri($C_1$-$C_8$)alkylsilyl-$C_1$-$C_8$-alkyl;

m represents 0, 1, 2 or 3;

$R^1$, $R^2$, $R^3$ and $R^4$ independently one to another represent hydrogen; halogen; $C_1$-$C_{16}$-alkyl; $C_2$-$C_{16}$-haloalkyl having 1 to 9 identical or different halogen atoms; $C_3$-$C_8$-cycloalkyl; $C_3$-$C_7$-halocycloalkyl having 1 to 9 identical or different halogen atoms; $C_1$-$C_6$-haloalkyl having 1 to 9 identical or different halogen atoms; ($C_3$-$C_8$-cycloalkyl)-$C_1$-$C_8$-alkyl; ($C_3$-$C_8$-cycloalkyl)-$C_3$-$C_8$-cycloalkyl; $C_2$-$C_{16}$-alkenyl; $C_2$-$C_{16}$-alkynyl; $C_2$-$C_{16}$-alkenyl-$C_1$-$C_{16}$-alkyl; $C_2$-$C_{16}$-alkynyl-$C_1$-$C_{16}$-alkyl; $C_1$-$C_{16}$-alkoxy; $C_3$-$C_8$-cycloalkyloxy; ($C_3$-$C_8$-cycloalkyl)-$C_1$-$C_8$-alkyloxy; $C_1$-$C_8$-alkylsulfanyl; $C_3$-$C_8$-cycloalkylsulfanyl; ($C_3$-$C_8$-cycloalkyl)-$C_1$-$C_8$-alkylsulfanyl; $C_2$-$C_{16}$-alkenyloxy; $C_3$-$C_8$-alkynyloxy; aryl which is optionally substituted by up to 6 identical or different groups $R^b$; aryl-$C_1$-$C_8$-alkyloxy which is optionally substituted by up to 6 identical or different groups $R^b$; aryl-$C_1$-$C_8$-alkylsulfanyl which is optionally substituted by up to 6 identical or different groups $R^b$; aryloxy which is optionally substituted by up to 6 identical or different groups $R^b$; arylsulfanyl which is optionally substituted by up to 6 identical or different groups $R^b$; ($C_3$-$C_8$-cycloalkyl)-$C_2$-$C_8$-alkenyl; ($C_3$-$C_8$-cycloalkyl)-$C_2$-$C_8$-alkynyl; tri($C_1$-$C_8$)alkylsilyl; tri($C_1$-$C_8$)alkylsilyl-$C_1$-$C_8$-alkyl; aryl-$C_1$-$C_8$-alkyl which is optionally substituted by up to 6 identical or different groups $R^b$; aryl-$C_2$-$C_8$-alkenyl which is optionally substituted by up to 6 identical or different groups $R^b$; aryl-$C_2$-$C_8$-alkynyl which is optionally substituted by up to 6 identical or different groups $R^b$;

provided that $R^1$, $R^2$, $R^3$ and $R^4$ do not simultaneously represent hydrogen or $R^1$ and $R^2$ represent together with the carbon to which they are attached a $C_3$-$C_8$-cycloalkyl; $C_3$-$C_8$-cycloalkenyl, each of which is optionally substituted or $R^1$ and $R^2$ represent a group $=C(Y^1)Y^2$ or $R^1$ and $R^2$ represent a 5 or 6 membered ring containing 1 or 2 heteroatoms or $R^3$ and $R^4$ represent together with the carbon to which they are attached a $C_3$-$C_8$-cycloalkyl, $C_3$-$C_8$-cycloalkenyl each of which is optionally substituted or $R^3$ and $R^4$ represent a group $=C(Y^1)Y^2$ or $R^3$ and $R^4$ represent a 5 or 6 membered ring containing 1 or 2 heteroatoms or $R^1$ and $R^3$ represent with the carbons to which they are attached a $C_3$-$C_8$-cycloalkyl, $C_3$-$C_8$-cycloalkenyl each of which is optionally substituted;

$R^b$ represents halogen; nitro, cyano, $C_1$-$C_{12}$-alkyl; $C_1$-$C_6$-haloalkyl having 1 to 9 identical or different halogen atoms; $C_1$-$C_6$-alkoxy; $C_1$-$C_6$-haloalkoxy having 1 to 9 identical or different halogen atoms; $C_1$-$C_6$-alkylsulfanyl; $C_1$-$C_6$-haloalkylsulfanyl having 1 to 9 identical or different halogen atoms; $C_1$-$C_6$-alkylsulfonyl; $C_1$-$C_6$-haloalkylsulfonyl having 1 to 9 identical or different halogen atoms; $C_2$-$C_{12}$-alkenyl; $C_2$-$C_{12}$-alkynyl; $C_3$-$C_7$-cycloalkyl; phenyl; tri($C_1$-$C_8$)alkylsilyl; or tri ($C_1$-$C_8$)alkylsilyl-$C_1$-$C_8$-alkyl;

$Y^1$ and $Y^2$ independently of one another represent hydrogen, halogen, $C_1$-$C_{12}$-alkyl; $C_1$-$C_6$-haloalkyl having 1 to 9 identical or different halogen atoms; $C_1$-$C_8$-alkylsulfanyl; phenyl; each of which is optionally substituted or $Y^1$ and $Y^2$ can form together with the carbon to which they are attached a $C_3$-$C_8$-cycloalkyl or a $C_3$-$C_8$-cycloalkenyl or a saturated 5, 6 or 7 membered heterocycle; each of which is optionally substituted.

2. Benzocyclobutane(thio) carboxamide of formula (I) according to claim 1 in which

Ar represents a radical selected from the group Ar1, Ar2, Ar4, Ar7, Ar8, Ar10 and Ar13;

$X^1$ represents halogen; $C_1$-$C_{16}$-alkyl, $C_1$-$C_6$-haloalkyl having 1 to 9 identical or different halogen atoms; $C_3$-$C_7$-cycloalkyl, or $C_3$-$C_7$-halocycloalkyl having 1 to 9 identical or different halogen atoms;

$X^2$, $X^3$, $X^4$ and $X^5$ independently from each other represent hydrogen, halogen, $C_1$-$C_{16}$-alkyl, $C_1$-$C_6$-haloalkyl having 1 to 9 identical or different halogen atoms; $C_3$-$C_7$-cycloalkyl, or $C_3$-$C_7$-halocycloalkyl having 1 to 9 identical or different halogen atoms;

T represents an oxygen atom;

Q represents hydrogen, $C_1$-$C_4$-alkylsulfonyl, $C_1$-$C_3$-alkoxy-$C_1$-$C_3$-alkyl, $C_1$-$C_4$-haloalkylsulfonyl, halo-$C_1$-$C_3$-alkoxy-$C_1$-$C_3$-alkyl having in each case 1 to 9 fluorine, chlorine or bromine atoms;

X represents fluorine, chlorine, methyl or trifluoromethyl;

m represents 0, 1 or 2;

$R^1$, $R^2$, $R^3$ and $R^4$ independently of one another represent hydrogen; halogen; $C_1$-$C_{16}$-alkyl; $C_2$-$C_{16}$-haloalkyl having 1 to 9 identical or different halogen atoms; $C_3$-$C_8$-cycloalkyl; $C_3$-$C_7$-halocycloalkyl having 1 to 9 identical or different halogen atoms; $C_1$-$C_6$-haloalkyl having 1 to 9 identical or different halogen atoms; ($C_3$-$C_8$-cycloalkyl)-$C_1$-$C_8$-alkyl; ($C_3$-$C_8$-cycloalkyl)-$C_3$-$C_8$-cycloalkyl; $C_1$-$C_{16}$-alkoxy; $C_3$-$C_8$-cycloalkyloxy; ($C_3$-$C_8$-cycloalkyl)-$C_1$-$C_8$-alkyloxy; aryl which is optionally substituted by up to 6 identical or different groups $R^b$; aryl-$C_1$-$C_8$-alkyloxy which is optionally substituted by up to 6 identical or different groups $R^b$; aryl-$C_1$-$C_8$-alkyl which is optionally substituted by up to 6 identical or different groups $R^b$;

provided that $R^1$, $R^2$, $R^3$ and $R^4$ do not simultaneously represent hydrogen or R$^1$ and R$^2$ represents together with the carbon to which they are attached an optionally substituted C$_3$-C$_8$-cycloalkyl where the substituents can be chosen from halogen and C$_1$-C$_6$-alkyl or R$^3$ and R$^4$ represents together with the carbon to which they are attached an optionally substituted C$_3$-C$_8$-cycloalkyl where the substituents can be chosen from halogen and C$_1$-C$_6$-alkyl or R$^1$ and R$^3$ represents together with the carbons to which they are attached an optionally substituted C$_3$-C$_8$-cycloalkyl where the substituents can be chosen from halogen and C$_1$-C$_6$-alkyl;

R$^b$ represents halogen; nitro, cyano, C$_1$-C$_8$-alkyl; C$_1$-C$_4$-haloalkyl having 1 to 9 identical or different halogen atoms; C$_1$-C$_6$-alkoxy; C$_1$-C$_4$-haloalkoxy having 1 to 9 identical or different halogen atoms; C$_1$-C$_6$-alkylsulfanyl; C$_1$-C$_4$-haloalkylsulfanyl having 1 to 9 identical or different halogen atoms; C$_1$-C$_6$-alkylsulfonyl; C$_1$-C$_4$-haloalkylsulfonyl having 1 to 9 identical or different halogen atoms; C$_2$-C$_8$-alkenyl; C$_2$-C$_8$-alkynyl; C$_3$-C$_6$-cycloalkyl; phenyl; tri(C$_1$-C$_6$)alkylsilyl; or tri(C$_1$-C$_6$)alkylsilyl-C$_1$-C$_6$-alkyl.

3. Benzocyclobutane(thio) carboxamide of formula (I) according to claim 1
in which
Ar represents a radical selected from the group Ar1, Ar2 and Ar4;
X$^1$ represents C$_1$-C$_{12}$-alkyl, C$_1$-C$_4$-haloalkyl having 1 to 9 identical or different halogen atoms;
X$^2$, X$^3$, X$^4$ and X$^5$ independently from each other represent hydrogen, fluorine, chlorine, bromine, iodine; C$_1$-C$_{12}$-alkyl, or C$_1$-C$_4$-haloalkyl having 1 to 9 identical or different halogen atoms;
T represents an oxygen atom;
Q represents hydrogen, methylsulfonyl, ethylsulfonyl, n- or isopropylsulfonyl, n-, iso-, sec- or tert-butylsulfonyl, methoxymethyl, methoxyethyl, ethoxymethyl, ethoxyethyl, trifluoromethylsulfonyl, or trifluoromethoxymethyl;
X represents fluorine
m represents 0 or 1;
R$^1$, R$^2$, R$^3$ and R$^4$ independently of one another represent hydrogen; halogen; C$_1$-C$_{16}$-alkyl; C$_2$-C$_{16}$-haloalkyl having 1 to 9 identical or different halogen atoms; C$_3$-C$_8$-cycloalkyl; C$_3$-C$_7$-halocycloalkyl having 1 to 9 identical or different halogen atoms; C$_1$-C$_6$-haloalkyl having 1 to 9 identical or different halogen atoms; (C$_3$-C$_8$-cycloalkyl)-C$_1$-C$_8$-alkyl; (C$_3$-C$_8$-cycloalkyl)-C$_3$-C$_8$-cycloalkyl; C$_1$-C$_{16}$-alkoxy; aryl which is optionally substituted by up to 6 identical or different groups R$^b$; aryl-C$_1$-C$_8$-alkyl which is optionally substituted by up to 6 identical or different groups R$^b$;
provided that R$^1$, R$^2$, R$^3$ and R$^4$ do not simultaneously represent hydrogen or
R$^1$ and R$^2$ represents together with the carbon to which they are attached an optionally substituted cyclopropyl, cyclobutyl, cyclopentyl, cyclohexyl where the substituents can be chosen from fluorine, chlorine, methyl and ethyl or
R$^3$ and R$^4$ represents together with the carbon to which they are attached an optionally substituted cyclopropyl, cyclobutyl, cyclopentyl, cyclohexyl where the substituents can be chosen from fluorine, chlorine, methyl and ethyl;
R$^b$ represents fluorine, chlorine, bromine; C$_1$-C$_6$-alkyl; C$_1$-C$_4$-haloalkyl having 1 to 9 identical or different halogen atoms; C$_1$-C$_4$-alkoxy; C$_1$-C$_4$-haloalkoxy having 1 to 9 identical or different halogen atoms; C$_1$-C$_4$-alkylsulfanyl; C$_1$-C$_4$-haloalkylsulfanyl having 1 to 9 identical or different halogen atoms; C$_1$-C$_4$-alkylsulfonyl; C$_1$-C$_4$-haloalkylsulfonyl having 1 to 9 identical or different halogen atoms; C$_2$-C$_6$-alkenyl; C$_2$-C$_6$-alkynyl; C$_3$-C$_6$-cycloalkyl; phenyl; tri(C$_1$-C$_4$)alkylsilyl; or tri(C$_1$-C$_4$)alkylsilyl-C$_1$-C$_4$-alkyl.

4. Benzocyclobutane(thio) carboxamide of formula (I) according to claim 1
in which
Ar represents a radical selected from the groups Ar2 and Ar4;
X$^1$ represents difluoromethyl;
X$^2$, X$^3$ and X$^4$ independently from each other represent fluorine or chlorine;
T represents an oxygen atom;
Q represents hydrogen;
m represents 0;
R$^1$, R$^2$, R$^3$ and R$^4$ independently of one another represent; hydrogen, phenyl, ethyl, methyl, or propan-2-yl;
provided that R$^1$, R$^2$, R$^3$ and R$^4$ do not simultaneously represent hydrogen or
R$^3$ and R$^4$ represents together with the carbon to which they are attached an optionally substituted cyclopentyl, or cyclohexyl.

5. A process for preparing one or more benzocyclobutane (thio) carboxamides of formula (I) according to claim 1, comprising reacting a compound of formula (II)

(II)

wherein Z represents halogen, cyano, hydroxyl or an activated hydroxyl group,
with a compound of formula (III-a)

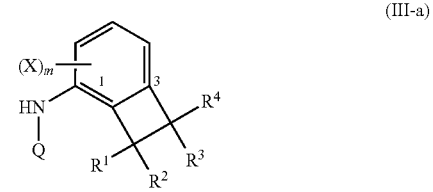

(III-a)

wherein the definitions are the same as those recited in claim 1,
to obtain one or more compounds of formula (I-a)

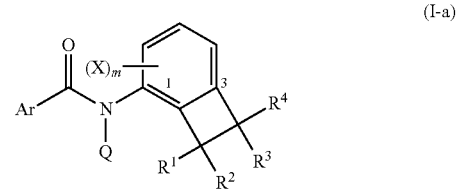

(I-a)

and in case that for the compounds according to formula (I) T represents sulfur, reacting one or more compounds of formula (I-a) in the presence of a thionating agent to obtain a compound of formula (I-b)

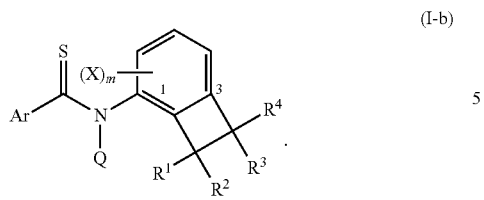
(I-b)

6. Composition for controlling phytopathogenic harmful fungi, comprising a content of at least one compound of formula (I) according to claim 1 and one or more extenders and/or surfactants.

7. Method for controlling phytopathogenic harmful fungi, comprising applying one or more compounds of formula (I) according to claim 1 to the phytopathogenic harmful fungi and/or a habitat thereof.

8. Process for producing a composition for controlling phytopathogenic harmful fungi, comprising mixing one or more compounds of the formula (I) according to claim 1 with one or more extenders and/or surfactants.

9. A method according to claim 7 comprising treatment of transgenic plants, seed or of seed of transgenic plants.

10. Benzocyclobutane(thio) carboxamide of formula (I) according to claim 1, wherein m represents 0.

11. Benzocyclobutane(thio) carboxamide of formula (I) according to claim 1, wherein m represents 1, 2 or 3.

12. Method for controlling phytopathogenic harmful fungi, comprising applying one or more compounds of formula (I) according to claim 4 to the phytopathogenic harmful fungi and/or a habitat thereof.

* * * * *